US009658221B2

(12) United States Patent
Liscidini et al.

(10) Patent No.: US 9,658,221 B2
(45) Date of Patent: May 23, 2017

(54) METHODS AND DEVICES FOR DETECTION OF ANALYTES USING BLOCH SURFACE WAVE-ENHANCED DIFFRACTION-BASED SENSORS

(75) Inventors: Marco Liscidini, Toronto (CA); John Sipe, Toronto (CA)

(73) Assignee: The Governing Council of the University of Toronto, Toronto (CA)

( * ) Notice: Subject to any disclaimer, the term of this patent is extended or adjusted under 35 U.S.C. 154(b) by 1504 days.

(21) Appl. No.: 13/061,424

(22) PCT Filed: Aug. 28, 2009

(86) PCT No.: PCT/CA2009/001192
§ 371 (c)(1),
(2), (4) Date: May 19, 2011

(87) PCT Pub. No.: WO2010/022512
PCT Pub. Date: Mar. 4, 2010

(65) Prior Publication Data
US 2011/0236998 A1 Sep. 29, 2011

Related U.S. Application Data

(60) Provisional application No. 61/190,431, filed on Aug. 28, 2008.

(51) Int. Cl.
| G01N 33/551 | (2006.01) |
| G01N 33/543 | (2006.01) |
| G01N 21/47 | (2006.01) |
| G01N 21/64 | (2006.01) |
| G01N 33/552 | (2006.01) |

(52) U.S. Cl.
CPC ... *G01N 33/54373* (2013.01); *G01N 21/4788* (2013.01); *G01N 21/648* (2013.01); *G01N 33/552* (2013.01)

(58) Field of Classification Search
None
See application file for complete search history.

(56) References Cited

U.S. PATENT DOCUMENTS

| 4,243,398 | A | * | 1/1981 | Nomura et al. | ................ 65/413 |
| 4,815,843 | A | * | 3/1989 | Tiefenthaler et al. | ........ 356/128 |
| 5,071,248 | A | * | 12/1991 | Tiefenthaler et al. | ........ 356/128 |
| 5,478,527 | A | * | 12/1995 | Gustafson et al. | ........ 422/82.11 |
| 5,907,436 | A | * | 5/1999 | Perry et al. | .................... 359/576 |
| 6,990,259 | B2 | * | 1/2006 | Cunningham | ......... B82Y 20/00 385/12 |
| 6,991,938 | B1 | | 1/2006 | Cookson et al. | |

(Continued)

OTHER PUBLICATIONS

Porter et al, "Rayleigh-Bloch surface waves along periodic gratings and their connection with trapped modes in waveguides", Journal of Fluid Mechanics, 1999, vol. 386, pp. 233-258.*

(Continued)

*Primary Examiner* — Chris L Chin
(74) *Attorney, Agent, or Firm* — Clark & Elbing LLP

(57) ABSTRACT

The invention features methods and diffraction-based devices for the detection of specific analytes. The devices of the invention contain a periodic dielectric multilayer, which allows for the propagation of Bloch surface waves (BSWs) at the surface of the multilayer, thereby increasing the sensitivity of the device.

32 Claims, 15 Drawing Sheets

(56) References Cited

U.S. PATENT DOCUMENTS

| | | | |
|---|---|---|---|
| 7,008,794 B2 | 3/2006 | Goh et al. | |
| 7,023,544 B2* | 4/2006 | Cunningham | B01L 3/5085 356/326 |
| 7,314,749 B2 | 1/2008 | Goh et al. | |
| 7,531,786 B2* | 5/2009 | Cunningham | B01L 3/5085 250/214.1 |
| 2003/0067687 A1* | 4/2003 | Barton et al. | 359/569 |
| 2005/0231806 A1* | 10/2005 | Barton et al. | 359/566 |
| 2006/0099649 A1 | 5/2006 | Goh et al. | |

OTHER PUBLICATIONS

Angeley et al., "Fabrication of an optical-quality linear grating of immunoglobulin G proteins by microcontact printing and demonstration of potential biosensing applications," Opt Eng. 45(4):043402 (2006).

Apfel., "Graphical method to design multilayer phase retarders," Appl Opt. 20(6):1024-9 (1981).

Apfel., "Phase retardance of periodic multilayer mirrors," Appl Opt. 21(4):733-8 (1982).

Astratov et al., "Photonic band-structure effects in the reflectivity of periodically patterned waveguides," Phys Rev B 60(24): R16255-58 (1999).

Burckhardt, "Efficiency of a Dielectric Grating," J Opt Soc Am. 57(5): 601-3 (1967).

Burckhardt, "Diffraction of a Plane Wave at a Sinusoidally Stratified Dielectric Grating," J Opt Soc Am. 56(11): 1502-9 (1966).

Darmawan et al., "Critical coupling, oscillation, reflection, and transmission in optical waveguide-ring resonator systems," J Opt Soc Am B. 23(5):834-41 (2006).

Descrovi et al., "Field localization and enhanced Second-Harmonic Generation in silicon-based microcavities," Opt Express. 15(7):4159-67 (2007).

Goh et al., "Diffraction-based assay for detecting multiple analytes," Anal Bioanal Chem. 374(1):54-6 (2002).

Liscidini et al, "Diffraction enhancement via Bloch surface waves in a-SiN:H multilayers," In: Conference on Lasers and Electro-Optics (CLEO). Baltimore, Maryland, May 31, 2009. JThE106. Edited by the Optical Society of America (2 pages), 2009.

Liscidini et al., "Analysis of Bloch-surface-wave assisted diffraction-based biosensors," J Opt Soc Am B. 26(2):279-89 (2009).

Liscidini et al., "Enhancement of diffraction for biosensing applications via Bloch surface waves," Appl Phys Lett. 91:253125(1-3) (2007).

Liscidini et al., "Second-harmonic generation in doubly resonant microcavities with periodic dielectric mirrors." Phys Rev E Stat Nonlin Soft Matter Phys. 73(1 Pt 2):016613(1-11) (2006).

Liscidini et al., "Enhancement of diffraction-based biosensor sensitivity via a Bloch surface wave," In: Conference on Lasers and Electro-Optics (CLEO). San Jose, California. May 4, 2008. JTuA58. Edited by the Optical Society of America (2 pages), 2008.

Ricciardi et al., "Amorphous Silicon Nitride: a suitable alloy for optical multilayered structures," J Non-Crystalline Solids. 352:1294-7 (2006).

Robertson et al., "Surface electromagnetic wave excitation on one-dimensional photonic band-gap arrays," Appl Phys Lett. 74(13):1800-02 (1999).

Yeh et al., "Optical surface waves in periodic layered media," Appl Phys Lett. 32(2):104-5 (1978).

Yu et al., "Immunosensor with self-referencing based on surface plasmon diffraction," Anal Chem. 76(7):1971-5 (2004).

Yu et al., "Surface plasmon enhanced diffraction for label-free biosensing," Anal Chem. 76(13):3530-5 (2004).

Whittaker et al., "Scattering-matrix treatment of patterned multilayer photonic structures," Phys Rev B. 60(4):2610-18 (1999).

Rong et al., "Nanoscale porous silicon waveguide for label-free DNA sensing," Biosens Bioelectron. 23(10):1572-6 (2008).

Wei et al., "Grating couplers on porous silicon planar waveguides for sensing applications," J Appl Phys. 104:123113(1-5) (2008).

Supplementary European Search Report for European Application No. 09809153.1, dated Aug. 23, 2011 (5 pages).

International Preliminary Report on Patentability for International Application No. PCT/CA2009/001192, mailed Mar. 10, 2011 (6 pages).

\* cited by examiner

METHODS AND DEVICES FOR DETECTION OF ANALYTES USING BLOCH SURFACE WAVE-ENHANCED DIFFRACTION-BASED SENSORS

CROSS-REFERENCE TO RELATED APPLICATIONS

This application claims benefit of U.S. Provisional Application No. 61/190,431, filed Aug. 28, 2008, which is hereby incorporated by reference.

BACKGROUND OF THE INVENTION

In general, this invention relates to the fields of Bloch surface wave-enhanced optical diffraction and analyte detection.

Optical devices play an important role in biosensing, offering high sensitivity, fast responses, and the capability of remote sensing. A change in the amplitude, phase, or frequency of an input beam in response to the presence of an analyte is used to alter detection, providing an optical transduction of the biorecognition process that often includes the adsorption or absorption of the analyte of interest. There are a number of optical effects that can be exploited in sensing, such as a modification of the fluorescence properties of the molecules involved in the detection or a simple local refractive index change due to the presence of the analyte. In diffraction-based sensors, the magnitude of signal typically depends on a change in the thickness of a grating, and this change is usually very small.

Accordingly, diffraction-based sensors with improved signal generation are desirable.

SUMMARY OF THE INVENTION

In general, the present invention features methods and diffraction-based devices for the detection of specific analytes. The devices of the invention contain a periodic dielectric multilayer, which allows for the propagation of Bloch surface waves (BSWs) at the surface of the multilayer, thereby increasing the sensitivity of the device, e.g., compared to a device without the multilayer.

Accordingly, the invention features a device that includes a diffraction grating, with an immobilized binding agent capable of binding to an analyte and a periodic dielectric multilayer, wherein Bloch surface waves are capable of propagating at the surface of the periodic dielectric multilayer, thereby enhancing diffraction from the grating. Exemplary binding agents include proteins (e.g., an antibody such as immunoglobulin G) or nucleic acids.

In a related aspect, the invention features a diffraction-based device having a diffraction grating having chemical groups capable of immobilizing a binding agent capable of binding to an analyte, and a periodic dielectric multilayer, wherein Bloch surface waves are capable of propagating at the surface of the periodic dielectric multilayer, thereby enhancing diffraction from the diffraction grating. This device allows the end user to specify the desired analyte by contacting the device with an appropriate binding agent, as described herein. Exemplary chemical groups include biotin, avidin, streptavidin, protein G, or amine-reactive groups.

Any of the devices described herein may further include a substrate layer, e.g., that is silicon-based. Any of the devices described herein may further include a prism base, e.g., for the Kretschmann configuration. The prism may be, for example, a zinc-selenium prism.

In any of the devices described herein, the periodic dielectric multilayer may contain between 2 and 20 periods (e.g., 2, 3, 4, 5, 6, 7, 8, 9, 10, 11, 12, 13, 14, 15, 16, 17, 18, 19, or 20 periods). Alternatively, the multilayer may include more than 20 periods. The multilayer of the device may also contain between 2 and 80 layers (e.g., 2, 3, 4, 5, 6, 7, 8, 9, 10, 15, 20, 25, 30, 35, 40, 45, 50, 55, 60, 65, 70, 75, or 80 layers). Alternatively, the multilayer may contain more than 80 layers. Each period may contain, e.g., between 1 and 40 layers (e.g., 1, 2, 3, 4, 5, 6, 7, 8, 9, 10, 15, 20, 25, 30, 35, or 40 layers). In a specific embodiment, the device of the invention includes 7 periods, each containing 2 layers.

In any of the devices described herein, the periodic dielectric multilayer may include layers containing silicon or silicon dioxide ($SiO_2$). The periodic dielectric multilayer may also include layers containing silicon nitride at a ratio of $Si_{(1-x)}N_x$:H (e.g., $Si_3N_4$:H or $Si_{0.45}N_{0.55}$:H). Other materials that may be used in any layer of the multilayer include, for example, zinc sulfide (ZnS), titanium oxide ($TiO_2$), cerium oxide ($CeO_2$), magnesium fluoride (MgF), cryolite ($Na_3AlF_6$), gallium nitride (GaN), indium tin oxide (ITO), zinc telluride (ZnTe), BeZnTe, MgSe/BeZnTe, InGaAs, indium phosphide (InP), gallium arsenide (GaAs), $Al_xGa_{1-x}$As, GaAsSb, or $Al_xGa_{1-x}$N. Other materials useful in the fabrication of optical quality thin films are known in the art and may also be used in any layer of the multilayer.

In a specific embodiment, the device of the invention has a first layer containing silicon nitride at a ratio of $Si_3N_4$:H and a second layer containing silicon nitride at a ratio of $Si_{0.45}N_{0.55}$:H. The periodic dielectric multilayer of the device may further include an additional layer that contains silicon nitride at a ratio of $Si_{0.45}N_{0.55}$:H. The thickness of the first layer may be about 150 nm; the thickness of the second layer may be about 140 nm; and the thickness of the additional layer may be about 42 nm. The actual thickness of the layers will depend on the refractive index of the layers.

The invention also features a method for the detection of an analyte in a sample by contacting a device of the invention with the sample and detecting a signal associated with the analyte binding to the immobilized binding agent on the surface of the device by Bloch surface wave-enhanced optical diffraction. When the device employed has chemical groups that immobilize a binding agent, the method may further include the step of first immobilizing the binding agent to the grating.

The invention also features a method for the detection of an analyte in a sample by contacting a device that includes a diffraction grating capable of binding the analyte with the sample and detecting a signal associated with the analyte binding to the diffraction grating on the surface of the device by Bloch surface wave-enhanced optical diffraction.

By "antibody" is meant monoclonal antibodies (including full-length monoclonal antibodies), polyclonal antibodies, multispecific antibodies, and antibody fragments. An antibody recognizes and binds an antigen, but does not substantially recognize or bind to other, unrelated molecules in a biological sample. Specific recognition of an antigen by an antibody may be assayed by using, e.g., light diffraction devices with an immobilized capture surface or using standard techniques known to one of skill in the art, such as immunoprecipitation, Western blotting, and ELISA.

By "analyte" is meant a protein, carbohydrate, nucleic acid, lipid, hapten, or other naturally occurring or synthetic compound. Preferably, the analyte is a protein or a complex of proteins. An analyte may be a biomarker.

By "binding affinity" is meant the strength of the total noncovalent interactions between a single binding site of a molecule (e.g., an antibody) and its binding partner (e.g., an antigen). Unless otherwise indicated, as used herein, "binding affinity" refers to intrinsic binding affinity, which reflects a specific interaction between members of a binding pair (e.g., antibody and antigen). The affinity of a molecule X for its partner Y can generally be represented by the dissociation constant ($K_d$). Affinity can be measured by standard methods known in the art, including those described herein. A low-affinity complex contains an antibody that generally tends to dissociate readily from the antigen, whereas a high-affinity complex contains an antibody that generally tends to remain bound to the antigen for a longer duration.

By "binding agent" is meant a molecule that has a binding affinity for another molecule. Binding agents include any substance capable of binding an analyte. The binding agent may be, e.g., a protein (e.g., an antibody, antigen, or fragment thereof) or a polynucleotide (e.g., an aptamer).

By "sample" is meant any biological or non-biological material used in a diagnostic or monitoring assay. The sample may be obtained from an individual (e.g., a subject). Exemplary samples include bones, teeth, seeds, plants, pathological or non-pathological animal tissue (e.g., muscle, liver, kidney, lung, brain, pancreas, prostate, ovary, breast, etc.), tumor tissue, rocks, mineral samples, or food products. Biological samples encompass, e.g., a clinical sample, cells in culture, cell supernatants, cell lysates, serum, plasma, biological fluid (e.g., urine), and tissue samples. The source of the sample may be solid tissue (e.g., from a fresh, frozen, and/or preserved organ or tissue sample or biopsy or aspirate), blood or any blood constituents, bodily fluids (such as, e.g., cerebral spinal fluid, amniotic fluid, peritoneal fluid, or interstitial fluid), or cells from any time in gestation or development of the individual. In some embodiments, the sample is obtained from a primary or metastatic tumor. The sample may contain compounds that are not intermixed with the tissue in nature, such as preservatives, anticoagulants, buffers, fixatives, nutrients, or antibiotics.

By "biomarker" is meant a molecule, other chemical species (e.g., an ion), or particle that is an indicator of a biologic (e.g., pathological or disease) state. Exemplary biomarkers include proteins (e.g., antigens or antibodies), carbohydrates, cells, viruses, nucleic acids, and small organic molecules. The biomarker may be a biomarker complex.

By "cancer" and "cancerous" is meant the physiological condition in mammals that is typically characterized by unregulated cell growth. Included in this definition are benign and malignant cancers, as well as dormant tumors or micro-metastases. Examples of cancer include, but are not limited to, carcinoma, lymphoma, blastoma, sarcoma, and leukemia. More particular examples of such cancers include, e.g., prostate cancer, squamous cell cancer, small-cell lung cancer, non-small-cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, vulval cancer, thyroid cancer, hepatic carcinoma, gastric cancer, melanoma, and various types of head and neck cancer.

By "cardiovascular disease" is meant a disease that affects the heart and/or blood vessels (e.g., veins and arteries). Exemplary cardiovascular diseases include angina, myocardial infarction (e.g., acute myocardial infarction), cardiac amyloidosis, cardiac contusions, defibrillation, coronary vasospasms, dilated cardiomyopathy, heart failure, hypertrophic cardiomyopathy, myocarditis, atherosclerosis, or supraventricular tachycardia.

By "disease" is meant any condition that may be diagnosed or screened for according to the methods of the invention described herein. Non-limiting examples of diseases to be diagnosed herein include, e.g., cardiovascular diseases (e.g., acute myocardial infarction), cerebrovascular diseases (e.g., stroke), cancers (e.g., malignant tumors, carcinomas, blastomas, and sarcomas), autoimmune diseases (e.g., autoimmune hepatitis, multiple sclerosis, systemic lupus erythematosus, myasthenia gravis, type I diabetes, rheumatoid arthritis, psoriasis, Hashimoto's thyroiditis, Grave's disease, Sjogren's syndrome, and scleroderma), and infections (e.g., hepatitis C or human immunodeficiency virus (HIV)).

By "immobilized" is meant bound directly or indirectly to a surface of, e.g., a device, including attachment by covalent binding or noncovalent binding (e.g., hydrogen bonding, ionic interactions, van der Waals forces, or hydrophobic interactions).

By "signal" is meant light intensity (e.g., light generated by fluorescence, bioluminescence, or phosphorescence), ionizing radiation, particle emission, magnetism, staining, or a product of a reaction involving an enzyme. Diffraction, absorbance, polarization, reflection, deflection, increases, decreases, or amplification of a signal may be indicative of an event (e.g., binding of an analyte to an antibody immobilized on the surface of a BSW-assisted diffraction-based device).

By "subject" is meant humans and other animals including, e.g., mice, rats, guinea pigs, hamsters, rabbits, cats, dogs, goats, sheep, cows, or monkeys.

Other features and advantages of the invention will be apparent from the following detailed description, the drawings, and the claims.

DETAILED DESCRIPTION OF THE INVENTION

The invention features methods and diffraction-based devices for the detection of specific analytes. The devices of the invention contain a periodic dielectric multilayer, which allows for the propagation of Bloch surface waves (BSWs) at the surface of the multilayer, thereby increasing the sensitivity of the device. The invention may be used for diagnosing disease and evaluating the efficacy of treatment.

Properties of Bloch Surface Waves

Figure 1:
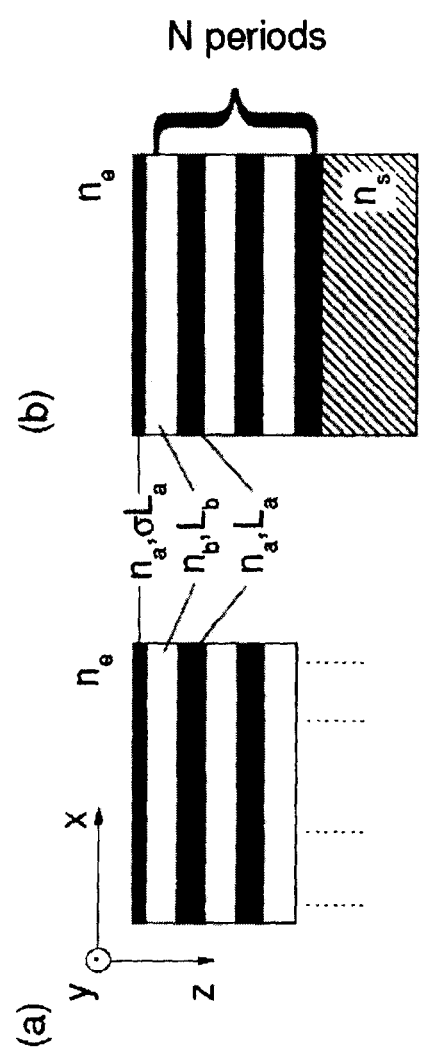
FIG. 1a is a diagram of a semi-infinite multilayer.
FIG. 1b is a diagram of a corresponding finite multilayer structure.

The performance of BSW-assisted diffraction-based sensors depends on the properties of surface waves in periodic dielectric stacks. The modes are characterized by strong field confinement at the interface between a truncated periodic multilayer and a semi-infinite homogeneous medium. These modes arise from reflectance due to a photonic band gap in a first medium and total internal reflection from a second medium. They can exist for transverse electric (TE) and transverse magnetic (TM) polarized fields, defined with respect to the xz plane, as indicated in FIG. 1. There are many methods to derive BSW dispersion relations. For example, mode polarization and the termination of the periodic structure may be used to derive the dispersion relations.

We consider a periodic structure with a unit cell composed of two layers of thickness L$_a$ and L$_b$ and refractive indices n$_a$ and n$_b$, respectively. The unit cell starts on the a side of an interface and ends in the next such location one lattice space away. The transfer matrix associated with the unit cell is:

$$M = \begin{pmatrix} M_{11} & M_{12} \\ M_{12}^* & M_{11}^* \end{pmatrix} = \Phi_a I_{ab} \Phi_b I_{ba},$$ [Equation 1]

where, in specifying the form of the components of M, we have assumed there is no loss (see, for example, Yariv et al., *Optical Waves in Crystals*, Wiley, N.J., 2003). Even more generally, $$\Phi_i = \begin{pmatrix} e^{iw_i L_i} & 0 \\ 0 & e^{-iw_i L_i} \end{pmatrix},$$ [Equation 2]

where $$w = \sqrt{\left(\frac{2\pi}{\lambda_0} n_i\right)^2 - k_x^2},$$ [Equation 3]

(Im$\sqrt{z}$≥0, with Re$\sqrt{z}$≥0 if Im$\sqrt{z}$=0) with λ$_0$ the wavelength in vacuum, and k$_x$ the component of the wave vector in the plane of the surface; the I$_{ij}$ are the interface matrices, $$I_{ij} = \frac{1}{t_{ij}} \begin{pmatrix} 1 & r_{ij} \\ r_{ij} & 1 \end{pmatrix},$$ [Equation 4]

where $r_{ij}$ and $t_{ij}$ are, respectively, Fresnel reflection and transmission coefficients from i to j, which depend on the field polarization. The eigenvectors of M satisfy the relation:

$$\begin{pmatrix} M_{11} & M_{12} \\ M_{12}^* & M_{11}^* \end{pmatrix} \begin{pmatrix} a_0 \\ b_0 \end{pmatrix} = e^{iKL} \begin{pmatrix} a_0 \\ b_0 \end{pmatrix},$$ [Equation 5]

where $L=L_a+L_b$ is the photonic crystal period and K the Bloch wavevector. For example, $$a_0 = M_{12} \text{ and } b_0 = e^{iKL} - M_{11}$$ [Equation 6].

The matrix M is identified with a unit cell starting at the a side of an interface, followed by thickness $L_b$ of index $n_b$, another interface, and thickness $L_a$ of index a. We can consider a more general choice of a unit cell, in which we begin with a first layer of index $n_a$ with thickness $L_1 = \sigma L_a$, where $\sigma \in [0, 1]$. This more general transfer matrix $M_\sigma$ is given by:

$$M_\sigma = \Phi_\sigma^{-1} \Phi_a I_{ab} \Phi_b I_{ba} \Phi_\sigma = \Phi_\sigma^{-1} M \Phi_\sigma$$ [Equation 7], where $\Phi_\sigma$ describes the field propagation in the first layer, $$\Phi_\sigma = \text{diag}(e^{iw_a \sigma L_a}, e^{-iw_a \sigma L_a})$$ [Equation 8].

We can then demonstrate that:

$$M_\sigma \begin{pmatrix} a_\sigma \\ b_\sigma \end{pmatrix} = e^{iKL} \begin{pmatrix} a_\sigma \\ b_\sigma \end{pmatrix}$$ [Equation 9]

with $$\begin{pmatrix} a_\sigma \\ b_\sigma \end{pmatrix} = \Phi_\sigma^{-1} \begin{pmatrix} a_0 \\ b_0 \end{pmatrix}.$$ [Equation 10]

That is, M and $M_\sigma$ are similar and, therefore, have the same eigenvalues. This is physically clear since the photonic band structure depends only on the matrix eigenvalues and is independent of the particular choice of a unit cell; it can be considered a bulk property of the photonic crystal. These properties result from the properties of the transfer matrix and the system periodicity and hold true even when the unit cell composition is more complicated.

The BSW dispersion relation is found by requiring the continuity of the field tangential components at the surface of the multilayer. These conditions can be expressed in terms of the interface matrix equation:

$$\begin{pmatrix} 0 \\ E_e^- \end{pmatrix} = \frac{1}{t_{ea}} \begin{pmatrix} 1 & r_{ea} \\ r_{ea} & 1 \end{pmatrix} \begin{pmatrix} a_\sigma \\ b_\sigma \end{pmatrix},$$ [Equation 11]

where $E_e^-$ is the amplitude of the evanescent field in the homogeneous medium; the vanishing of the first component of the vector arises from the condition on a surface excitation that it can exist without the presence of an incident field, here from medium e. From this equation, we extract:

$$a_\sigma + r_{ea} b_\sigma = 0$$ [Equation 12]

or $$\frac{b_0}{a_0} r_{ae} e^{iw_a \sigma L_a} = 1,$$ [Equation 13]

where we used the identity $r_{ea} = -r_{ae}$. The ratio ($b_0/a_0$) is the complex reflectance coefficient for the semi-infinite multilayer viewed from medium a. This permits the description of different multilayer terminations using the phase factor $e^{iw_a \sigma L_a}$, where the variation of the first layer thickness appears explicitly. The Fresnel reflection coefficients can now be specified when all of the refractive indices are real. For example, $$r_{ae}^{TE} = \frac{w_a - w_e}{w_a + w_e} = \frac{w_a - iq_e}{w_a + iq_e},$$ [Equation 14]

$$r_{ae}^{TE} = \frac{\varepsilon_e w_a - \varepsilon_a w_e}{\varepsilon_e w_a + \varepsilon_a w_e} = \frac{\varepsilon_e w_a - i\varepsilon_a q_e}{\varepsilon_e w_a + i\varepsilon_a q_e},$$ [Equation 15]

where $\in_i = n_i^2$ is the dielectric function in the medium i, and $q_e$ is defined through:

$$q_e \equiv -iw_e = \sqrt{k_x^2 - \left(\frac{2\pi}{\lambda_0} n_e\right)^2},$$ [Equation 16]

where the solutions of Equations 12 or 13 have the root argument of $q_e$ is positive. Substitution of these expressions in Equation 13 yields:

$$q_e^{(TE)} = iw_a \frac{a_\sigma^{(TE)} - b_\sigma^{(TE)}}{a_\sigma^{(TE)} + b_\sigma^{(TE)}}$$ [Equation 17]

$$q_e^{(TE)} = iw_a \frac{a_\sigma^{(TE)} - b_\sigma^{(TE)} e^{2iw_a \sigma L_a}}{a_\sigma^{(TE)} + b_\sigma^{(TE)} e^{2iw_a \sigma L_a}}$$

$$q_e^{(TE)} = iw_a \frac{M_{12}^{(TE)} e^{-2iw_a \sigma L_a} + M_{11}^{(TE)} e^{iK^{(TE)}L}}{M_{12}^{(TE)} e^{-2iw_a \sigma L_a} - M_{11}^{(TE)} e^{iK^{(TE)}L}}$$

and $$q_e^{(TM)} = i\omega_a \frac{\varepsilon_e a_\sigma^{(TM)} - b_\sigma^{(TM)}}{\varepsilon_a a_\sigma^{(TM)} + b_\sigma^{(TM)}}$$ [Equation 18]

$$q_e^{(TM)} = iw_a \frac{\varepsilon_e M_{12}^{(TM)} e^{-2iw_a \sigma L_a} + M_{11}^{(TM)} e^{iK^{(TM)}L}}{\varepsilon_a M_{12}^{(TM)} e^{-2iw_a \sigma L_a} - M_{11}^{(TM)} e^{iK^{(TM)}L}},$$

for TE and TM polarization, respectively. The sign of the imaginary part of K must be taken as negative to guarantee field exponential decay in the multilayer. The relation of Equation 16 with Equations 17 and 18 gives the equation:

$$q_e^{TM(TE)} = \sqrt{k_x^2 - \left(\frac{2\pi}{\lambda_0} n_e\right)^2},$$ [Equation 19]

which is equivalent to Equations 12 and 13. These results can be generalized to the case in which the unit cell structure is more complicated. Solutions to Equation 19 correspond to the poles of the structure reflectance coefficient viewed from the external medium and must be found numerically in the ($k_x$, $\omega$) plane, where $\omega$ is the mode frequency. At a fixed $\omega$, for real refractive indices, one can find the roots by solving Equation 19 using bracketing and bisection or Newton-Raphson methods (Press et al., *Numerical Recipes: The Art of Scientific Computing*, Third Edition, Cambridge University Press, Cambridge, 2007). The search interval is limited to the gap region and, in general, more than one state can be found (Yariv et al., *Optical Waves in Crystals*, Wiley, N.J., 2003). These equations hold even in the case of complex refractive indices. There, the BSW wave vectors $k_x$ at fixed real ω are complex, and the search for solutions of Equation 19 is more complicated. See, e.g., Example 1.

Diffraction-Based Biosensing with BSWs

Figure 2:
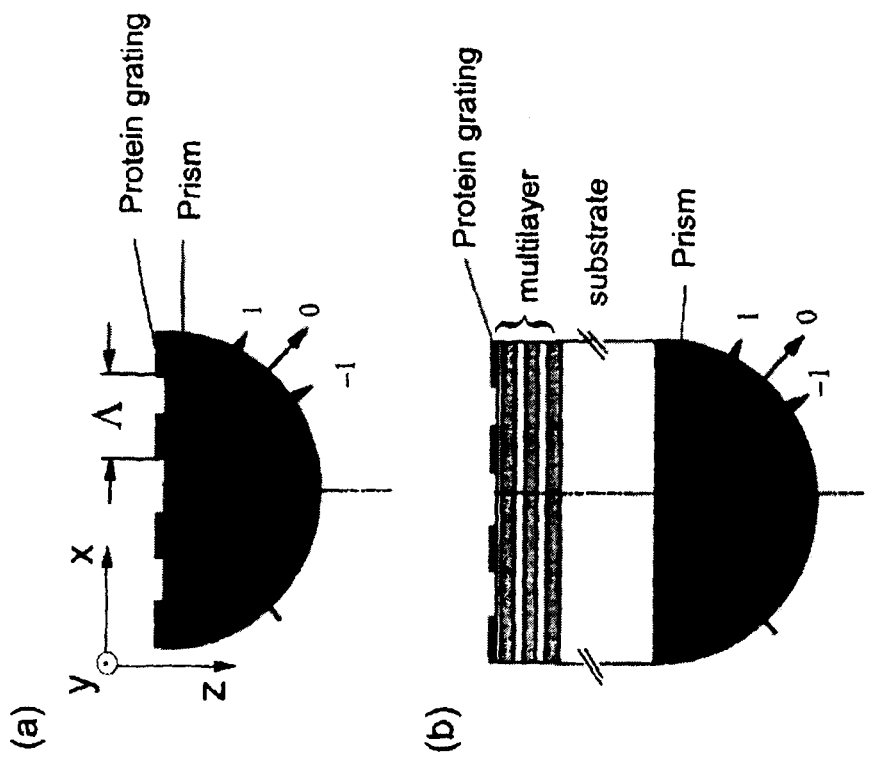
FIG. 2a is a diagram of a simple diffraction-based sensor in the Kretschmann configuration.
FIG. 2b is a diagram of a Bloch surface wave-assisted diffraction-based sensor in the Kretschmann configuration.

The recognition component of the diffraction-based sensor of the present invention includes, for example, a one-dimensional grating of period Λ composed of binding agents (e.g., a protein (e.g., an antibody, antigen, or fragment thereof) or polynucleotide molecule) capable of binding a specific analyte (see, e.g., Goh et al., *Anal Bioanal Chem.* 374: 54, 2001 and Angeley et al., *Optical Engineering* 45: 043402, 2006). FIG. 2*a* shows a sketch of a traditional version of such a diffraction-based sensor. The grating is formed on top of a prism and both excitation and detection are performed in the Kretschmann configuration. This allows for sensing in the total internal reflection regime of both incident and diffracted beams, limiting light interaction with the biological material to the grating region and maximizing diffraction in the lower half-space where it is most easily measured. If the grating height d is much smaller than the wavelength λ of the incident beam, the intensity of the m-th order diffracted beam is $$I_m \propto I_{Inc}\eta(k_x)\eta(k_d = k_x + mG)\left(\frac{\pi(\Delta n)d}{2\lambda}\right)^2 \quad \text{[Equation 20]}$$

$$m \in Z,$$

where Δn is the refractive index contrast in the grating region, $I_{Inc}$ the incident field intensity, and $k_x$ and $k_d$ are the wave vector components of the incident and diffracted beam along the grating periodicity direction $\hat{x}$, respectively (see, e.g., FIG. 2). The minimum grating momentum contribution is $G=2\pi/\Lambda$, while $\eta(k_x)$ and $\eta(k_x+mG)$ describe the efficiency with which the incident and diffracted beam propagate in the structure for a given polarization. When the analyte is immobilized on the detector surface, the grating thickness and the fraction of light diffracted increases. The analyte is detected by monitoring the diffraction signal, which depends quadratically on the grating optical contrast (Δn)d (Yu et al., *Anal Chem.* 76: 1971, 2004 and Yu et al., *Anal Chem.* 76: 3530, 2004). In particular, if we assume that η is independent of the analyte concentration, and hence of d, a small change δξ of the optical thickness (Δn)d produces a variation of the diffracted intensity:

$$\frac{\delta I_m}{\delta \xi} \propto I_{Inc}\eta(k_x)\eta(k_d)\left(\frac{\pi(\Delta n)d}{2\lambda}\right). \quad \text{[Equation 21]}$$

Despite the fact that $\delta I_m/\delta\xi$ depends linearly on the incident intensity, the optical thickness of the grating, and the coefficients $\eta(k_x)$ and $\eta(k_d)$, not all of these dependencies can be exploited effectively to improve device performance. For instance, in principle one could increase the sensitivity of a device employing a simple, inexpensive laser by two or three orders of magnitude by using instead a laser that was much more intense. However, this would require an expensive light source that may not be easy to operate. One could also employ a larger initial grating, increasing (Δn)d in Equation 21. Here, one would be limited by the fact that Equations 20 and 21 hold in the limit d<<λ (Burckhardt, *J Opt Soc Am.* 56: 1502, 1966 and Burckhardt, *J Opt Soc Am.* 57: 601, 1967).

Two more useful strategies for improving device performance are to design a structure such that (1) light is better localized at the surface or (2) a better extraction of the diffracted field is achieved. These conditions can be satisfied, respectively, when the incident or diffracted beams are resonant with a mode of the structure that is characterized by a strong field confinement in a region close to the grating. They correspond to maximizing $\eta(k_x)$ and $\eta(k_x+mG)$, respectively. The introduction of a thin metal layer between the grating and the prism may be used to take advantage of the large field localization associated with a surface plasmon (Yu et al., *Anal Chem.* 76: 1971, 2004 and Yu et al., *Anal Chem.* 76: 3530, 2004). This solution yields important benefits in terms of diffraction enhancement (Liscidini et al., *Appl Phys Lett.* 91: 253125, 2007). Nevertheless, it requires long period gratings (~100 μm) to ensure coupling of the diffracted beam with the surface plasmon and prevent its absorption. In this situation, since G<<$k_x$, the diffracted beam is almost collinear to the reflected one and its detection can be difficult.

Another possible route is exploiting a Bloch surface wave. Here, the field is confined by total internal reflection on one side and by the photonic gap on the other side. In many ways, the BSW can be considered a dielectric version of a surface plasmon, even though there are two important differences. First, while the field confinement associated with a surface plasmon in a metal results from a negative dielectric function, the field exponentials' decay in the multilayer of a BSW-assisted diffraction-based device is the result of a destructive interference in the photonic band gap, and the constituent materials can be transparent and lossless. Second, while a surface plasmon requires a TM polarized field, a BSW can exist for both TE and TM polarizations. In FIG. 2*b*, we show a sketch of the sensor, where the grating is formed on the top of a periodic multilayer that is grown on a substrate. The BSW is excited in the Kretschmann configuration, and diffraction is collected through the prism. The light is coupled into the BSW mode through the prism and, thus, the grating acts only as a biosensing element. The performance and flexibility of a BSW sensor, compared to usual surface plasmon sensors, are related to the fact that dielectric stacks can be free from absorption losses. Another important advantage is the capability of tailoring the position of the photonic gap and the surface state by means of a careful design of the multilayer. This solution is suitable for many different materials and high reflectivity mirrors can be realized even when the refractive index contrast is small.

Limitations on the performance of surface plasmon-assisted devices typically arise because one cannot avoid absorption losses in metallic systems, which set a limit to the maximum field enhancement and, in diffraction-based sensors, lead to the choice of long periods. In these systems, there exists an optimal thickness of the metallic layer that ensures the largest diffraction efficiency. The thickness determination is the result of a compromise between the field enhancement, which is stronger with thicker metal layers, and the absorption of incident and diffracted beam, which increases exponentially with the metal thickness. In diffraction-based sensors where BSW are exploited, it is possible to choose materials that are transparent at the working wavelength. The field enhancement in this system is related to the reflectivity of the multilayer, which depends on the unit cell composition, the refractive index contrast, and the number N of periods.

On the other hand, diffraction represents a loss for the surface mode and, thus, limits the BSW "quality factor." There must be a critical coupling between incoming beam and BSW so that the diffraction enhancement is at a maximum. Thus, the coupling issues in BSW sensors are qualitatively different than in plasmon structures. While the loss that typically dominates the calculation for surface plasmon structures is incidental and detrimental to the detection process, the essential loss in BSW sensors is associated with the detection process. However, there are analogs between the BSW sensor and other sensors.

Figure 14:
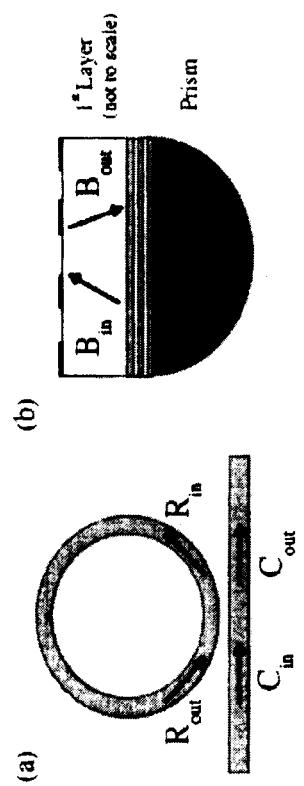
FIG. 14a is a diagram of a one-channel ring resonator configuration.
FIG. 14b is a diagram of Bloch-surface wave excitation in Kretschmann configuration. The first layer is not to scale.

To understand the critical coupling issue, we relied on an analogy with a one-channel ring resonator in this example, characterized by a certain number of losses in the ring region, which could be considered due to an analyte. In the ring structure, there is a critical coupling between the channel and the ring that leads to the quenching of the transmitted signal in the output port (see, e.g., FIG. 14$a$) (Darmawan et al., $J$ $Opt$ $Soc$ $Am$ $B$ 60: 2610, 1999). This is analogous to the quenching of the reflected beam in the sensor of the present invention due to diffraction. To establish the analogy and construct equations for this system that mimic those of the resonator structure, we considered the situation depicted in FIG. 14$b$. The BSW was excited by an incident beam of amplitude $A_{inc}$ that propagated in the structure up to the multilayer surface and then was totally reflected at the interface. For the benefit of illustration, the thickness of the layer closest to the surface was deliberately exaggerated in FIG. 14$b$. The ring output channel $C_{out}$ corresponds to the channel $A_{ref}$ in the BSW structure. As in the case of the ring, BSW field enhancement depends on the coupling strength, which is, in the absence of losses, governed by the minor reflectivity. Using a simple transfer matrix formalism, $$\begin{pmatrix} A_{inc} \\ A_{ref} \end{pmatrix} = \begin{pmatrix} \frac{1}{t^*} & \frac{r^*}{t^*} \\ \frac{r}{t} & \frac{1}{t} \end{pmatrix} \begin{pmatrix} B_{in} \\ B_{out} \end{pmatrix}, \quad \text{[Equation 22]}$$

where r and t are the complex reflectance and transmittance coefficients of the multilayer. In the hypothesis of total internal reflection at interface with the external medium, the field amplitudes at the surface are related by the simple relation:

$$B_{out} = B_{in} e^{i\phi(\omega)} \quad \text{[Equation 23]}$$

where $\phi(\omega)$ is a phase delay that depends on the nature of the interface with the external medium and the layer thickness. Thus, the reflectance of the whole structure can be written:

$$R_{tot} = |\tilde{r}|^2 = \left|\frac{A_{ref}}{A_{inc}}\right|^2 = \left|\frac{1 + r e^{-i\phi}}{e^{-i\phi} + r^*}\right|^2, \quad \text{[Equation 24]}$$

where $\tilde{r}$ is the total complex reflectance coefficient. In absence of losses, $R_{tot}=1$ and BSW structure reflectance corresponds to the ring structure transmittance. In the case of a diffraction-based sensor, the presence of the grating introduces a loss term for the channel $A_{ref}$. We took into account the diffraction losses by introducing a phenomenological dissipation term in Equation 23:

$$B_{out} = B_{in} e^{-\beta(d)} e^{i\phi(\omega)} \quad \text{[Equation 25]},$$

where $\beta>0$ describes the diffraction losses and it is a function of the grating thickness d. It is worth noting that we were not considering the case in which the diffraction depends strongly on the structure properties at $k_d$; that is, the only resonance effects are on the incoming beam. When these effects are small or negligible, we see, as described below, that this picture clarifies the existence of a critical coupling and gives a reasonable prediction of the total diffraction efficiency. In order to simplify our calculations, we introduced the following notation:

$$r = \sqrt{R} e^{i\psi_r} = \rho e^{i\psi_r} \quad \text{[Equation 26]}$$

where $\rho$ and $\tau$ comprise the mirror reflectance module and $\psi_r$ the corresponding phase. The expression for $R_{tot}$ in the case of losses is:

$$R_{tot} = \left|\frac{1 + \rho e^{\beta} e^{i(\psi_r - \psi_i - \phi)}}{\rho e^{-i\psi_r} - e^{\beta} e^{-i\phi}}\right|^2 \quad \text{[Equation 27]}$$

$$R_{tot} = \left|\frac{1 + \rho e^{\beta} e^{i(\psi_r - \phi)}}{\rho e + e^{\beta} e^{i(\psi_r - \phi)}}\right|^2 \quad \text{[Equation 28]}$$

$$R_{tot} = \left|\frac{1 + \rho e^{\beta} e^{i\Delta}}{\rho + e^{\beta} e^{i\Delta}}\right|^2 \quad \text{[Equation 29]}$$

$$R_{tot} = \frac{1 + \rho^2 e^{2\beta} + 2\rho e^{\beta} \cos(\Delta)}{\rho^2 + e^{2\beta} + 2\rho e^{\beta} \cos(\Delta)}, \quad \text{[Equation 30]}$$

where $\Delta = \psi_r - \phi$ is the total phase shift. When we are resonant with BSW, the total phase shift is equal to $(2m+1)\pi$, with m being an integer. In this case, the system reflectance is:

$$R_{BSW}(\rho, \beta) = \frac{1 + \rho^2 e^{2\beta} - 2\rho e^{\beta}}{\rho^2 + e^{2\beta} - 2\rho e^{\beta}} = \left(\frac{1 - \rho e^{\beta}}{\rho - e^{\beta}}\right)^2. \quad \text{[Equation 31]}$$

When the losses are small, the resonance condition is still the one predicted by Equation 19. The resonance position also depends on the number of periods that define the multilayer phase reflectance. As the number of periods increases, the structure properties and thus the position of the BSW converges to the value predicted for the semi-infinite system (Apfel, $Appl$ $Opt$. 20: 1024, 1981; Apfel, $Appl$ $Opt$. 21: 733, 1982; and Liscidini et al., $Phys$ $Rev$ $E$ 73: 016613, 2006). When the system is free from loss, the total diffraction is simply given by:

$$D_{BSW} = 1 - R_{BSW} = 1 - \left(\frac{1 - \rho e^{\beta}}{\rho - e^{\beta}}\right)^2. \quad \text{[Equation 32]}$$

We can also write an expression in which the grating thickness and the number of periods appear explicitly. It is sufficient to observe that the multilayer reflectance scales exponentially with N, and that for a thin grating $\beta$ is small and proportional to $d^2$. We write:

$$D_{BSW} = 1 - \left(\frac{1 - (1 - e^{-KLN})(1 + \gamma d^2)}{(1 - e^{-KLN}) - (1 + \gamma d^2)}\right)^2, \quad \text{[Equation 33]}$$

where the exponential is expanded in a Maclaurin series and only the first order term in $\beta$ is considered. Here, $\gamma$ is a parameter that describes the grating efficiency. We then considered the system discussed in Example 2 composed of a grating (n=1.45) in water (n=1.33) fabricated on an a-Si$_{0.45}$N$_{0.55}$/a-Si$_3$N$_4$ multilayer. In FIG. 16, we plotted the calculated total diffraction as a function of the number of periods N of the dielectric stacks obtained by means of a Fourier modal method and the curve evaluated through Equation 25 taking KL=0.51, where K is the BSW mode Bloch-vector, and using $\gamma d^2$ as a tuning parameter. An agreement between numerical and analytical results is obtained for $\gamma d^2=10^{-4}$, which is compatible with the diffraction efficiency value for the same grating placed directly onto the prism. This confirms the validity of Equations 24-25 when enhancement effects on diffraction extraction are small or negligible. The largest diffraction (~90%) is obtained for N=20. In diffraction-based sensors, one is typically focused on a specific diffraction order rather than the total diffraction efficiency, which is more difficult to measure.

Figure 15:
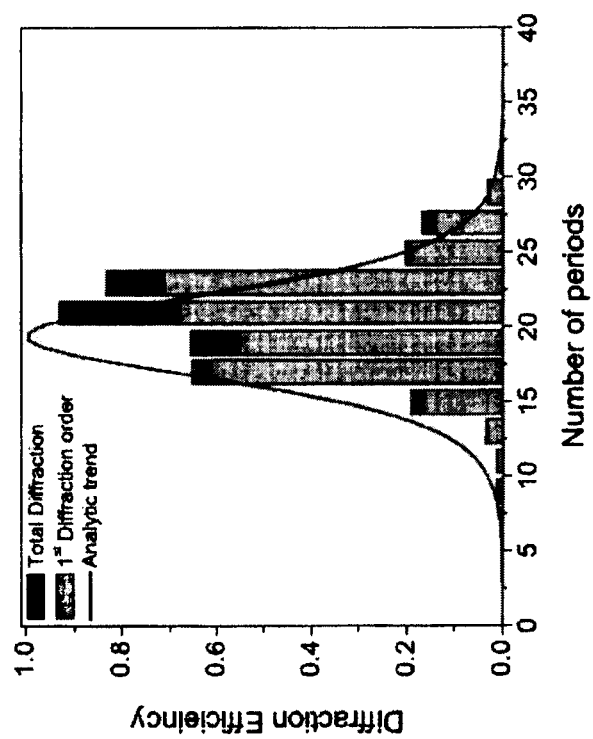
FIG. 15 is a plot showing the calculated total diffraction efficiency versus the number of periods N. The line represents the analytic trend; the boxes represent the numerical calculation. The portion of light scattered in the first diffraction order (with m=−1) is indicated by light gray boxes. The system is composed of a grating (n=1.45) of height d=4 nm in water (n=1.33) disposed onto a-Si$_{1-x}$N$_x$:H multilayer on a Corning 7059 (n=1.55) substrate. The unit cell is composed of 140 nm of a-Si$_{0.45}$N$_{0.55}$:H and 150 nm of a-Si$_3$N$_4$:H on a Corning 7059 substrate (n=1.55). The first layer is 42 nm of Si$_{0.45}$N$_{0.55}$. We assume TE polarized incident light. In the analytical calculation, KL=0.51 and β=γd$^2$=10$^{-4}$.

In FIG. 15, we also report the first diffraction order intensity corresponding to m=−1. The trend for m=−1 is very close to that for the total diffracted light. Light was diffracted from a one-dimensional grating mainly in the lower diffraction orders and, for our structure, the m=1 order was strongly reduced because, for the incident light at resonance with the BSW, that order lies below the Corning 7059 light line and propagation in the substrate is forbidden. However, we observed that the percentage of light that is scattered in the first order will be different for different N values. This reflected the fact that the extraction efficiency for a given order m, which is related to the structure properties at $k_d = k_x + mG$, is a function of N. The highest diffraction efficiency was not necessarily the design target for diffraction-based sensors. Too high of a diffraction efficiency could lead to saturation of the diffraction signal at analyte concentrations lower than desired and extremely high quality factors of the structure could lead to resonances too narrow for easy coupling.

Analytes and Binding Agents

Exemplary analytes include biomolecules (e.g., proteins, (e.g., antibodies or antigens)), hormones, metabolites, DNA, RNA, microRNA, polynucleotides and their analogs, lipids, toxins, or drugs, as well as larger assemblies, such as a virion or cell. The analyte may be, for example, a biomarker. The analyte may be, e.g., a complex or a component of a complex. For example, the complex may be a cardiac troponin complex, a PSA-ACT complex, a CK-MB complex, a MRP8/MRP14 complex, or a MMP-2/TIMP-2 complex. The analyte or analyte complex may contain multiple epitopes. For example, the analyte complex may be a multimer composed of single subunits, wherein the single subunits can be different isoforms that are modified, e.g., by alternative splicing, posttranslational modification, or degradation. Examples include protein forms that are cleaved, truncated (e.g., N-terminal or C-terminal truncations), phosphorylated, acetylated, alkylated, methylated, demethylated, formylated, or glycosylated.

The analytes to be detected may be present in a sample (e.g., blood, serum, plasma, crude cell lysates, urine, or a non-biological sample).

The methods and kits of the present invention allow for the detection of an analyte for, e.g., the diagnosis of a disease.

Various concentrations of analytes may be detected and measured by the methods described herein. Analytes present at concentrations less than, e.g., 100 milligrams/milliliter (mg/ml), 10 mg/ml, 1 mg/ml, 100 micrograms/milliliter (μg/ml), 10 μg/ml, 1 μg/ml, 100 nanograms/milliliter (ng/ml), 10 ng/ml, 1 ng/ml, 100 picograms/milliliter (pg/ml), 10 pg/ml, 1 pg/ml, 100 femtograms/milliliter (fg/ml), or 10 fg/ml may be detected in the biological sample, and the concentration may be measured.

Binding Agents

Binding agents include any substance capable of binding an analyte or component of an analyte complex. The binding agent may be, e.g., a protein (e.g., an antibody, antigen, or fragment thereof) or a polynucleotide. The polynucleotide may possess sequence specificity for the analyte or may be an aptamer.

An exemplary binding agent is an antibody that specifically binds to an analyte (e.g., an antigen). The binding agent used in the invention will ultimately depend on the analyte being assayed. The number of binding agents used in the invention described herein may be 1, 2, 3, 4, 5, 6, 7, 8, 9, 10, or more binding agents. The binding agent(s) may be, e.g., applied to the surface of the device of the invention.

Immobilized binding agents are present on the surface of the devices described herein. The immobilized binding agent may bind covalently or noncovalently to the surface of the devices by methods known to one of skill in the art, such as a biotin-avidin or biotin-streptavidin interaction, a Protein G interaction, a goat anti-mouse Fc interaction, an amide bond, or through any other covalent or noncovalent interaction.

Exemplary immobilized binding agents used in the devices of the invention may be agents that are, e.g., magnetic, positively charged, negatively charged, polarized, or capable of forming temporary dipoles, hydrogen bonds, van der Waals interactions, or hydrophobic interactions, so that the immobilized binding agent can bind to analytes in a sample by noncovalent means. Other immobilized binding agents include, e.g., charged polymers, hydrophobic polymers, and carbohydrates.

Methods to Detect and Measure an Analyte in a Biological Sample

The signal produced upon the binding of an analyte to the device of the invention described herein may be detected or measured using any technique known in the art, including, e.g., optical diffraction. Exemplary techniques for detection are provided in, e.g., U.S. Pat. No. 6,991,938, hereby incorporated by reference.

Methods for using optical diffraction-based assays will be known to those skilled in the art and are described in, e.g., U.S. Pat. Nos. 7,008,794 and 7,314,749, U.S. Patent Application Publication No. 2006/0099649, and in Goh et al. ("Diffraction-Based Assay for Detecting Multiple Analytes," *Anal. Bioanal. Chem.* 374: 54-56, 2002), which are hereby incorporated by reference.

Diffraction-based assays can involve immobilizing a binding agent (e.g., a protein (e.g., an antibody) or nucleic acid) in a distinct pattern on the surface of a device to create a diffraction grating. The binding agents are immobilized in distinct locations or assay spots on the surface of a device. The immobilized binding agents within each spot are not randomly distributed, but are immobilized in a pattern (e.g., a series of parallel lines) that produces a diffraction pattern when illuminated with a light (e.g., light with a wavelength in the range from the ultraviolet to the infrared, but preferably a coherent and collimated light beam, such as would come from a laser (e.g. diode, He—Ne, Nd:YVO$_4$, or Argon-ion lasers)).

Once the binding agent is immobilized on the multilayered device, the biological sample to be assayed is introduced into the device (e.g., by flowing the sample through the device), allowing the analytes present in the sample to bind to their binding agent on the surface of the device. When a particular analyte is present in the biological sample being tested, the subsequent binding event between the analyte and its complementary binding agent is accompanied by a change in the local thickness of the surface of the device and/or in the local index of refraction. Since diffraction gratings are typically only a few nanometers in thickness, the fraction of light that is diffracted is usually very small. In order to increase grating diffraction efficiency and improve device sensitivity, the device of the present invention exploits field enhancement associated with Bloch surface waves in a periodic dielectric multilayer, leading to enhanced diffraction from the diffraction grating at the surface of the device.

Since the diffraction-based detection of binding events is dependent on the pattern of the immobilized binding agents, an increase in signal occurs only when analytes bind selectively to those immobilized binding agents. Non-specific binding to the surface of the devices employed by the invention generally produces little or no change in the diffraction signal. This label-free characteristic of the invention enables the direct study of multiple analyte epitopes or analyte complex interactions in parallel, including, e.g., protein-protein interactions, nucleic acid-nucleic acid interactions, and nucleic acid-protein interactions. The methods of the invention also allow for the direct study of multiple analytes in a given biological sample.

Detection of the diffraction signal depends on the source of illumination. The detector may be, e.g., a position-sensitive photodiode, a photomultiplier tube (PMT), a photodiode (PD), an avalanche photodiode (APD), a charged-coupled device (CCD) array, the unaided eye, a camera, a photographic plate, or any other imaging device. The detector may be attached to the appropriate accessories to provide power and enable signal collection and data processing.

Devices

The device of the present invention includes a diffraction grating at the surface of the device and a periodic dielectric multilayer. The multilayer may be, e.g., a semi-infinite $Si/SiO_2$ multilayer. The periodic dielectric multilayer may further or alternately contain one or more layers of silicon nitride. The silicon nitride may be at a ratio of, for example, $Si_{(1-x)}N_x$:H (e.g., $Si_3N_4$:H or $Si_{0.45}N_{0.55}$:H). Other materials that may be used in any layer of the multilayer include zinc sulfide (ZnS), titanium oxide ($TiO_2$), cerium oxide ($CeO_2$), magnesium fluoride (MgF), cryolite ($Na_3AlF_6$), gallium nitride (GaN), indium tin oxide (ITO), zinc telluride (ZnTe), BeZnTe, MgSe/BeZnTe, InGaAs, indium phosphide (InP), gallium arsenide (GaAs), $Al_xGa_{1-x}As$, GaAsSb, or $Al_xGa_{1-x}N$. Other materials useful in the fabrication of optical quality thin films are known in the art and may be employed in multilayers.

The multilayer may contain, e.g., between 2 and 80 layers (e.g., 2, 3, 4, 5, 6, 7, 8, 9, 10, 15, 20, 25, 30, 35, 40, 45, 50, 55, 60, 65, 70, 75, or 80 layers). Alternatively, the multilayer may contain more than 80 layers. The multilayer may include, for example, between 2 and 20 periods (e.g., 2, 3, 4, 5, 6, 7, 8, 9, 10, 11, 12, 13, 14, 15, 16, 17, 18, 19, or 20 periods). Alternatively, the multilayer may include more than 20 periods. Each period may contain, e.g., between 1 and 40 layers (e.g., 1, 2, 3, 4, 5, 6, 7, 8, 9, 10, 15, 20, 25, 30, 35, or 40 layers). In a specific embodiment, the periodic dielectric multilayer includes a first layer of $Si_{0.45}N_{0.55}$:H 42 nm in thickness. This first layer is atop a multilayer of 7 periods, wherein each period contains 2 layers (e.g., a first layer of $Si_3N_4$:H 150 nm in thickness and a second layer of $Si_{0.45}N_{0.55}$:H 140 nm in thickness). Each layer may be between 1 to 500 nm in thickness (e.g., 1, 5, 10, 15, 20, 25, 30, 35, 40, 45, 50, 75, 100, 150, 200, 250, 300, 350, 400, 450, or 500 nm). The multilayer is transparent with an optical density of, for example, less than 0.1 at the wavelength of light employed, e.g., visible or IR. The multilayer may be built upon a substrate layer (e.g., a silicon substrate or Coming substrate). The substrate layer may be, for example, between 1 to 500 nm in thickness (e.g., 1, 5, 10, 15, 20, 25, 30, 35, 40, 45, 50, 75, 100, 150, 200, 250, 300, 350, 400, 450, or 500 nm). The thickness of the substrate layer and each layer of the multilayer depend on the refractive index of these layers.

The device used in the BSW-assisted diffraction-based assays described herein may be a flow-through device, i.e., having a liquid channel through which a sample, wash buffers, and other reagents may be passed. The diffraction patterns on the surface of the device may be created through any suitable technique, for example, microlithography, microcontact printing, inkjet writing, robotic spotting, dip pen nanolithography, nanolithograpahy by atomic force microscopy, or near-field optical scanning lithography. Components of the device not necessary for BSW-assisted diffraction may be made of any suitable material (e.g., a synthetic polymer (e.g., polystyrene), glass, metal, silicon, or semiconductor). Depending on the choice of material, the device employed may be disposable.

The surface of the device may be coated with different immobilized binding groups known in the art. Immobilized avidin groups on the surface of the device may be used for high-affinity immobilization of biotinylated binding agents (e.g., biotinylated antigens, biotinylated antibodies, or biotinylated polynucleotides). For example, a biotinylated antigen that specifically binds to an antibody is immobilized on the surface of an avidin-coated device. Protein G on the surface of the device binds to the Fc region of immunoglobulin molecules, allowing oriented immobilization of antibodies as binding agents on the surface of the device. Goat anti-mouse-Fc (GAM-Fc)-coated surfaces bind to the Fc region of mouse antibodies, also allowing oriented immobilization of binding agents, e.g., mouse antibodies, on the surface of the device employed by the invention. Immunoglobulin G (IgG) may also be bound to the surface of the device.

Immobilized carboxylate groups on an amine-reactive surface may be used to covalently link binding agents (e.g., with amide bonds) to the device's surface via an amine-coupling reaction. Other exemplary reactive linking groups, e.g., hydrazines, hydroxylamines, thiols, carboxylic acids, epoxides, trialkoxysilanes, dialkoxysilanes, and chlorosilanes may be attached to the surface of the device, such that binding agents may form chemical bonds with those linking groups to immobilize them on the surface of the device.

See, for example, Liscidini et al., *Appl Phys Lett.* 91: 253125, 2007, hereby incorporated by reference.

Uses of the Invention

The invention described herein features methods for detection of any analyte, e.g., for diagnosing disease and evaluating the efficacy of treatment of a subject with a disease or for monitoring environmental or other samples. Physicians and researchers may use the methods of the invention described herein to detect analytes or analyte complexes (e.g., cardiac biomarkers (e.g., troponins), tumor antigens, antibodies against tumor antigens, or lipoproteins), to diagnose or screen for disease (e.g., cardiovascular diseases (e.g., acute myocardial infarction), cancer, or autoimmune diseases), or to detect naturally occurring immune complexes in patient samples. Samples are typically in liquid form, but gaseous samples may also be employed.

Diagnosis of Diseases

The methods described herein may be used to diagnose diseases (e.g., acute myocardial infarction) in a subject. A physician or researcher may diagnose the disease based on, e.g., the presence or concentration of an analyte (e.g., a biomarker or biomarker complex (or components thereof)) indicative of the disease in a biological sample. The disease being diagnosed may be a cardiovascular disease (e.g., acute myocardial infarction); a cerebrovascular disease (e.g., stroke); cancer (e.g., a carcinoma, lymphoma, blastoma, sarcoma, or leukemia); an autoimmune disease; or infection (e.g., viral infections). More particular examples of such cancers include, e.g., prostate cancer, squamous cell cancer, small-cell lung cancer, non-small-cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, vulval cancer, thyroid cancer, hepatic carcinoma, gastric cancer, melanoma, and various types of head and neck cancer. Examples of autoimmune disease include autoimmune hepatitis, multiple sclerosis, systemic lupus erythematosus, myasthenia gravis, type I diabetes, rheumatoid arthritis, psoriasis, Hashimoto's thyroiditis, Grave's disease, Sjogren's syndrome, or scleroderma. Examples of infections include hepatitis C infection and human immunodeficiency virus (HIV) infection.

Monitoring the Efficacy of Treatment

The methods described herein may be used to monitor the efficacy of treatment of a disease of a subject. Such an evaluation includes, e.g., obtaining at least one biological sample from the subject before treatment begins, as well as obtaining at least one biological sample from the subject at a later time, e.g., any time after commencement of the treatment (e.g., 1, 2, 3, 4, 5, or 6 days; 1, 2, or 3 weeks; 1, 2, 3, 4, 5, 6, 7, 8, 9, 10, or 11 months; or 1, 2, 3, 4, or 5 years after treatment has begun). The pre- and post-treatment samples may then be applied to a device containing an immobilized binding agent (e.g., an antibody) that is capable of specifically binding to an analyte (e.g., a biomarker or biomarker complex (or component thereof)) associated with the disease of the subject. The devices generate signals that may be evaluated to determine the presence, absence, or concentration of a particular analyte. The efficacy of treatment may then be evaluated by comparing the composition of the analyte in each sample. For example, a decrease in the concentration of the analyte in the sample obtained after treatment had commenced may be an indication that the treatment of the disease is efficacious.

Methods of the invention may also be used to monitor the amount or concentration of analytes (e.g., biomarkers) in patients not undergoing treatment, e.g., to monitor disease progression.

The methods of the invention speed the detection of an analyte in a number of ways, including, e.g., quantifying analyte concentration and purity, characterizing binding kinetics, determining specificity and cross-reactivity, optimizing analyte concentrations, step times, buffers, and additive composition, monitoring assay performance and matrix effects, and multiplexing analytes with minimized interference.

EXAMPLES

The present invention is illustrated by the following examples, which are in no way intended to be limiting of the invention.

EXAMPLE 1

BSW Dispersion Relations of Semi-infinite and Infinite Periodic Structures

Mode polarization and the termination of the periodic structure may be used to derive dispersion relations. In addition, if the electric field is confined to the surface of the multilayer, only a few periods arc required for efficiently exploiting BSWs for biosensing applications.

Figure 3:
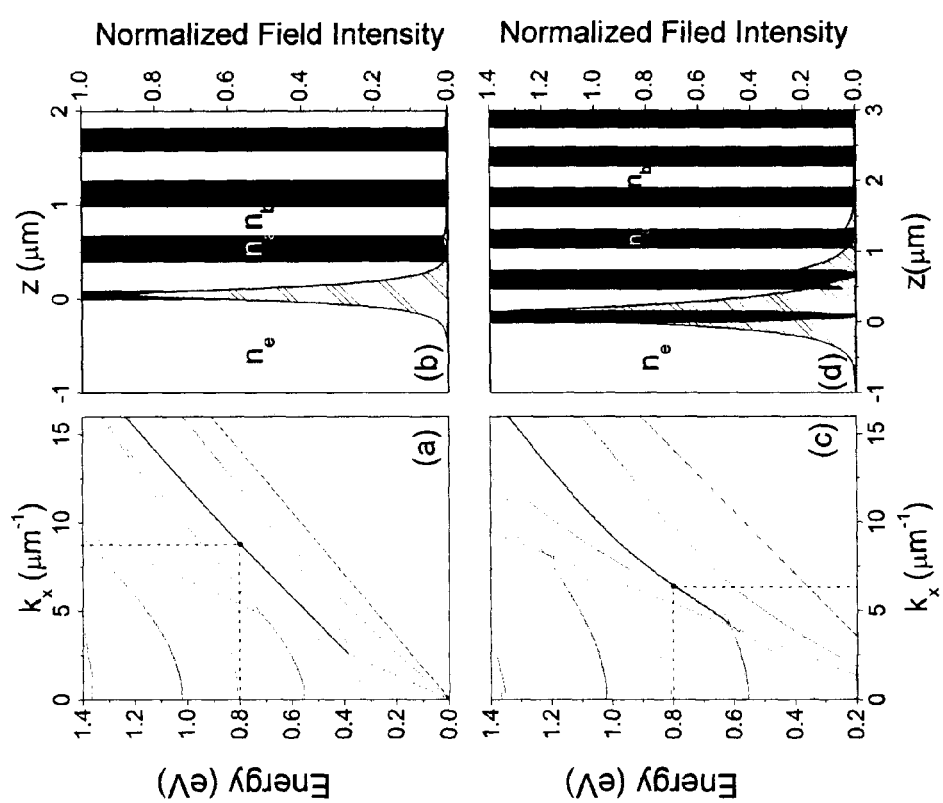
FIG. 3a is a plot of the photonic band and BSW dispersions for a semi-infinite periodic Si/SiO$_2$ multilayer with $L_a$=260, $n_a$=3.48 (Si), $L_b$=320, $n_b$=1.44 (SiO$_2$), σ=0.348, and $n_e$=1.33 (H$_2$O) for TE polarized light. Light lines for water and silicon are shown.
FIG. 3b is a plot of the field distribution in the multilayer for TE BSW at ω=0.8 (eV) and $k_x$=8.8 µm$^{-1}$.
FIG. 3c is a plot of the photonic band and BSW dispersions for the same semi-infinite periodic Si/SiO$_2$ multilayer but with σ=0.6 for TM polarized light. Light lines for water and silicon are shown.
FIG. 3d is a plot of the field distribution in the multilayer for TM BSW at ω=0.8 (eV) and $k_x$=6.5 µm$^{-1}$.

FIG. 3a shows the dispersion relation of the TE-polarized BSW for a semi-infinite Si/SiO$_2$ multilayer with $L_a$=260 (Si), $n_a$=3.48 (Si), $L_b$=320 (SiO$_2$), $n_b$=1.44 (SiO$_2$), $\sigma$=0.348, and $n_e$=1.33 (H$_2$O) for TE polarized light. Also shown is the light line of the external medium (e.g., water). FIG. 3b shows the field distribution for the mode at 0.8 eV (1.55 μm), which corresponds to $k_x$=8.8 μm. As expected, the field is strongly peaked at the interface between the multilayer and water. Once $k_x$ is fixed, the exponential decay in the homogeneous medium is determined by the refractive index $n_e$ through Equation 16. However, the attenuation in the multilayer depends on refractive index contrast, polarization, and multilayer termination that control the position of the mode within the photonic gap. Thus, in FIG. 3c, we show the TM BSW dispersion for the same periodic structure, but with a termination characterized by $\sigma$=0.6. The field distribution at 0.8 eV (1.55 μm) with $k_x$=6.3 μm is plotted in FIG. 3d. In this example, the BSW is closer to the photonic band-edge, and the field extends into the structure more deeply than is seen in FIG. 3b. The electric field is not continuous at the interfaces between different layers, and the electric field is typically much more intense where the dielectric function is smaller due to the strong electric field component normal to the surface that characterized the TM modes.

We have considered semi-infinite periodic structures, but, in practice, we must use a finite multilayer, such as the one depicted in FIG. 1b. Here, the dielectric stack is grown on a substrate with refractive index $n_s$. The rapid drop-off of the fields in FIGS. 3b and 3d indicates that, at least in such examples, the dispersion relations of BSW in semi-infinite structures can be used to understand the dispersion relations in finite structures, if the number N of periods of a finite structure is not too small. In this example, we confirm that if the field is confined to the surface, a few periods is sufficient. Indeed, it has been reported that for a Si/SiO$_2$ structure, an agreement between the dispersion relation evaluated for a semi-infinite system and a finite multilayer can be obtained even for N=2+½. Nonetheless, the nature of the BSW and the possibility of efficiently exploiting it for biosensing applications can be strongly influenced by substrate choice.

Figure 4:
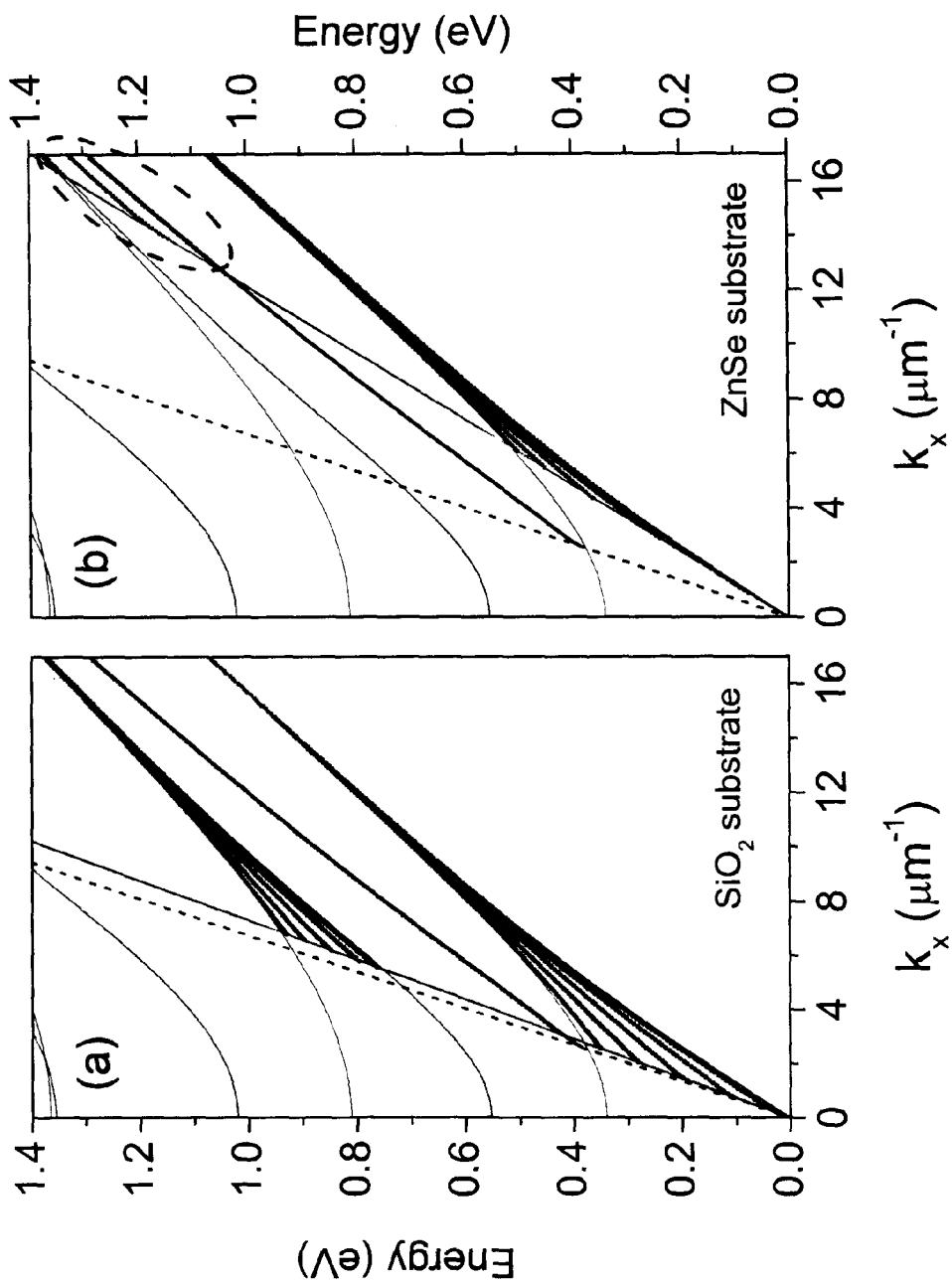
FIG. 4a is a plot of the photonic band and BSW dispersions for a semi-infinite periodic Si/SiO$_2$ multilayer with $L_a$=260, $n_a$=3.48 (Si), $L_b$=320, $n_b$=1.44 (SiO$_2$), σ=0.348, and $n_e$=1.33 (H$_2$O). Points are the poles of the reflectance coefficient for the corresponding finite structures composed of 5+½ periods on a SiO$_2$ substrate.
FIG. 4b is a plot of the photonic band and BSW dispersions for the same structure of FIG. 4a. Points are the poles of the reflectance coefficient for the corresponding finite structures composed of 5+½ periods on a ZnSe substrate. Light lines for external medium and substrate are shown.

In FIGS. 4a and 4b, we compare the dispersion relation of a TE BSW in a semi-infinite Si/SiO$_2$ periodic multilayer with the guided mode dispersion relations of the corresponding finite structures composed of 5+½ periods, but with different substrates. In the first example (FIG. 4a), we consider a low-index substrate, SiO$_2$. Below the upper and lower cladding light lines, the structure is a multilayer waveguide, and its mode dispersion relations can be found by identifying the poles of the structure transmittance or reflectance coefficients. The poles are plotted in FIG. 4a for TE polarization. We found several guided modes, among which the TE BSW is identifiable since it lies within the photonic band gap. Its dispersion relation coincides with that of the semi-infinite periodic structure, showing that, in this case, the BSW dispersion relation is not significantly affected by the silica substrate or finite size effects. In the second example (FIG. 4b), we consider the same multilayer on a ZnSe substrate, which has a larger refractive index ($n_{ZnSe}$=2.4). Here, a large part of the multilayer band gap lies above the light line of the substrate, and the BSW that would be a guided mode in a structure with a semi-infinite multilayer structure becomes a leaky surface mode. Guided modes exist only below the ZnSe light line in the region indicated on FIG. 4b by the ellipse. In particular, we find two distinct modes within the gap at $k_x$ above about 12 $\mu m^{-1}$. One mode has essentially the same dispersion relation of the BSW at the interface between water and the semi-infinite system and in the finite system is an extension of the leaky surface mode to the region of higher $k_x$ where guided modes can exist. The other mode, slightly higher in energy, is a guided mode localized at the interface between the multilayer and the substrate. Its dispersion relation could still be found to good approximation using Equation 19, but by considering an interface between the semi-infinite multilayer and ZnSe. For excitation in the Kretschmann configuration, the excitation of this surface mode is not limited by substrate thickness, since at such $k_x$ the electromagnetic field can propagate there. Attempts to use the guided modes would be limited by the fact that their electromagnetic fields are evanescent in the substrate and, although coupling into them through a higher index prism would be possible, it would limit the possible thickness of the substrate to a value small enough that fabrication might be difficult.

EXAMPLE 2

Diffraction-Based Biosensing with Bloch Surface Waves

We describe the construction of a BSW-assisted diffraction-based sensor. The biorecognition component of the diffraction-based sensor consists of a one-dimensional grating of period Λ, composed of molecules capable of binding a specific analyte. FIG. 2a is a diagram of a traditional version of such a diffraction-based sensor in the Kretschmann configuration. The grating is formed on top of a prism, and both excitation and detection are performed in the Kretschmann configuration. This allows for sensing in the total internal reflection regime of both incident and diffracted beams, limiting light interaction with the biological material to the grating region and maximizing diffraction in the lower half-space where it is most easily measured.

The sensor of the present invention exploits Bloch surface waves. Here, the field is confined by total internal reflection on one side and by the photonic gap on the other side. FIG. 2b shows a diagram of a BSW-assisted diffraction-based sensor, where the grating is formed on the top of a periodic multilayer that is grown on a substrate. The BSW is excited in the Kretschmann configuration, and diffraction is collected through the prism. Light is coupled into the BSW mode through the prism, and, thus, the grating acts only as a bio-sensing element.

Figure 5:
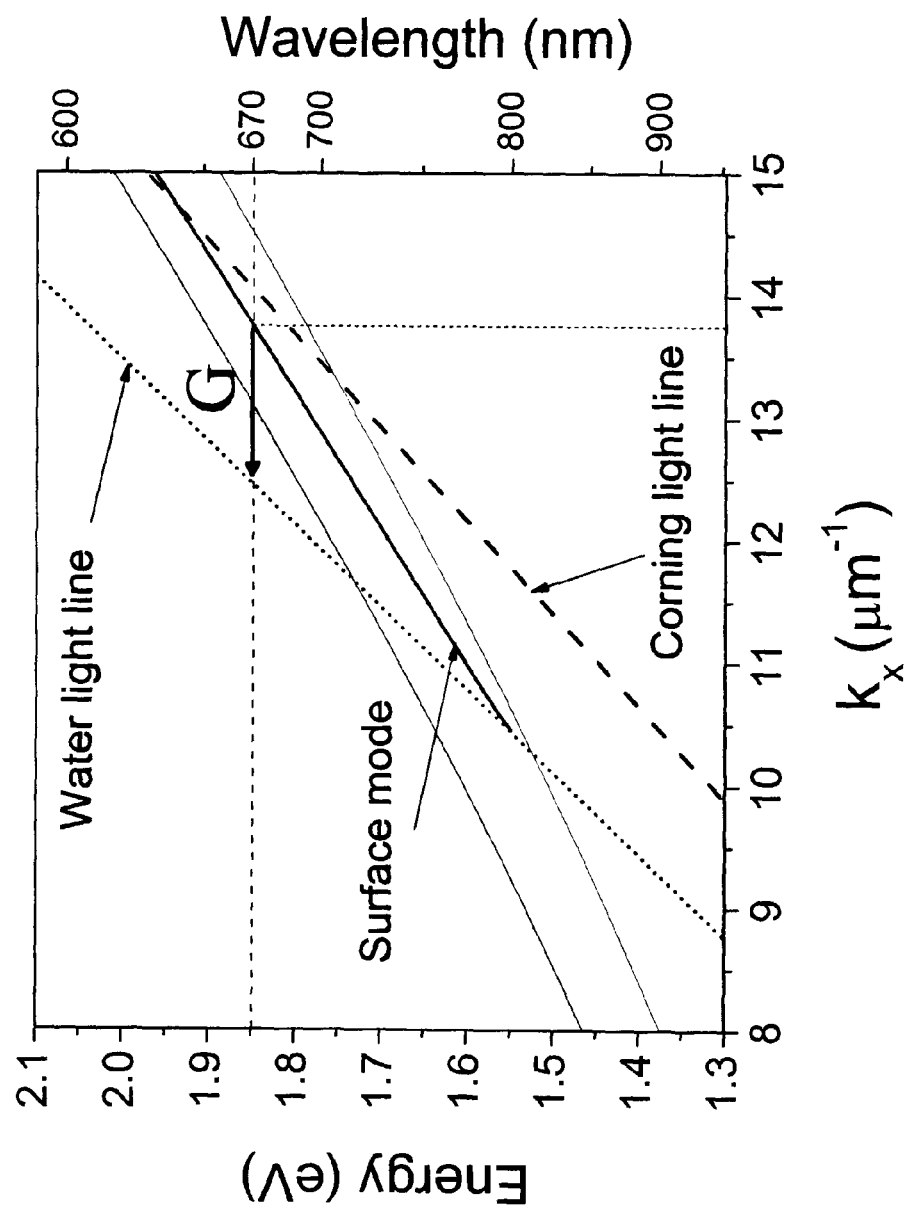
FIG. 5 is a diagram of TE Bloch surface wave dispersion for a-Si$_{1-x}$N$_x$:H multilayer. The unit cell is composed of 140 nm of a Si$_{0.45}$N$_{0.55}$:H and 150 nm of a-Si$_3$N$_4$:H. The first layer is 42 nm of a-Si$_{0.45}$N$_{0.55}$:H. The external medium is water (n=1.33). The vector G represents the momentum provided by a one-dimensional grating of period Λ=5 μm. Light lines for water and Corning substrate (n=1.55) are shown.

We designed a BSW-assisted diffraction-based sensor with a-$Si_{1-x}N_x$:H structure, where the refractive index is tuned by changing the nitrogen concentration x, and for which absorption in the visible range is small for x>0.5 (Descrovi et al., *Opt Express* 15: 4159, 2007 and Ricciardi et al., *J Non-Crystalline Solids* 352: 1294, 2006). It was important to identify a set of criteria that could be used in the design of a high-performance sensor of this type. First, a resonance with a BSW was sought for either an incoming or diffracted beam. Second, the incoming and diffracted beams should propagate in the substrate, so the device is operated above the substrate light line. Third, diffraction should occur in a specific order. For a one-dimensional grating, the first orders (m=±1) are usually the most intense, but one can adjust the photonic gap and light lines to privilege only one of them at a time. Finally, the diffracted beam should suffer total internal reflection at the interface with the external medium (e.g., water) to maximize the diffracted signal back through the substrate. FIG. 5 shows the dispersion relation of the TE-polarized BSW in the first photonic gap for a semi-infinite a-$Si_{0.45}N_{0.55}$:H/a-$Si_3N_4$:H periodic multilayer, where the external medium is taken to be water ($n_{H_2O}$=1.33). The unit cell is composed of 140 nm a-$Si_{0.45}N_{0.55}$ (n=1.96) and 150 nm a-$Si_3N_4$(n=1.78). The dielectric stack is truncated so that the first layer is 42 nm of a-$Si_{0.45}N_{0.55}$. We chose x>0.5, so the multilayer is transparent at λ=670 nm (1.851 eV). Because the refractive index contrast is so small (Δn~0.18), we have a small gap compared to the $Si/SiO_2$ multilayers (see, e.g., FIG. 3 or 4). The parameters of the multilayer have been chosen to maximize the diffraction efficiency of the order corresponding to m=−1. FIG. 5 shows the substrate light line, corresponding to a typical substrate for a-$Si_{1-x}N_x$:H, Corning 7059 ($n_s$=1.55). Also shown in FIG. 5 is the momentum contribution −G provided by a 5-µm period grating, typical in biosensing structures (Angeley et al., *Optical Engineering* 45: 043402, 2006). For our parameter choice, the surface mode at 670 rim was within the gap and above the substrate light line. The diffracted beam was in the region between the water light line and the upper band-edge, for which propagation in the multilayer is allowed. The mode position allowed for sample growth and grating fabrication. In this example, the prism and substrate were made of the same material.

Figure 6:
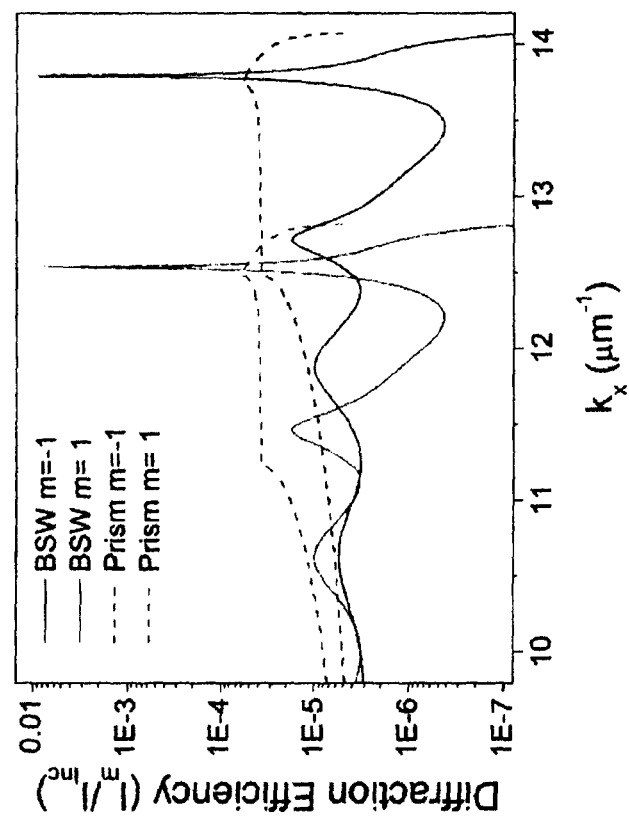
FIG. 6 is a plot of the calculated diffraction efficiency (I$_m$/I$_{Inc}$) for a 4 nm thick grating onto a-Si$_{1-x}$N$_x$:H multilayer with N=10 and a Corning 7059 prism (n=1.55) as a function of the incident light wave vector component k$_x$. The unit cell is composed of 140 nm of a-Si$_{0.45}$N$_{0.55}$:H and 150 nm of a-Si$_3$N$_4$:H on a Corning 7059 substrate (n=1.55). The first layer is 42 nm of Si$_{0.45}$N$_{0.55}$. We assume TE polarized incident light.

We compared the performance of this structure as a sensor with one in which the same grating (thickness d=4 nm and refractive index $n_{grating}$=1.45) was placed on a simple silica prism. Here, we considered the first diffraction orders (e.g., m=±1) for TE-polarized light. FIG. 6 shows the diffraction efficiencies calculated by means of a Fourier modal method as a function of the incident beam wavevector component $k_x$ (Whittaker et al., *Phys Rev B* 60: 2610, 1999). In the case of a simple prism, the response is almost independent of the angle of incidence, except for Wood anomalies associated with the grating. Contrary to the case of the simple prism, we found two strong peaks for the multilayer structure that corresponded to the excitation of the BSW by the incident beam (for m=−1) and by the diffracted beam (for m=+1). The distance between the two peaks (and also the distance between the Wood anomalies) was exactly 1.25 $\mu m^{-1}$, which corresponded to the momentum contribution provided by the grating of period 5 µm. The diffraction enhancement for this structure (N=10) periods was almost two orders of magnitudes. While we have assumed the prism has the same refractive index as the substrate, a prism of a large refractive index could be utilized to obtain a smaller angle of incidence and a simpler experimental set-up.

Figure 7:
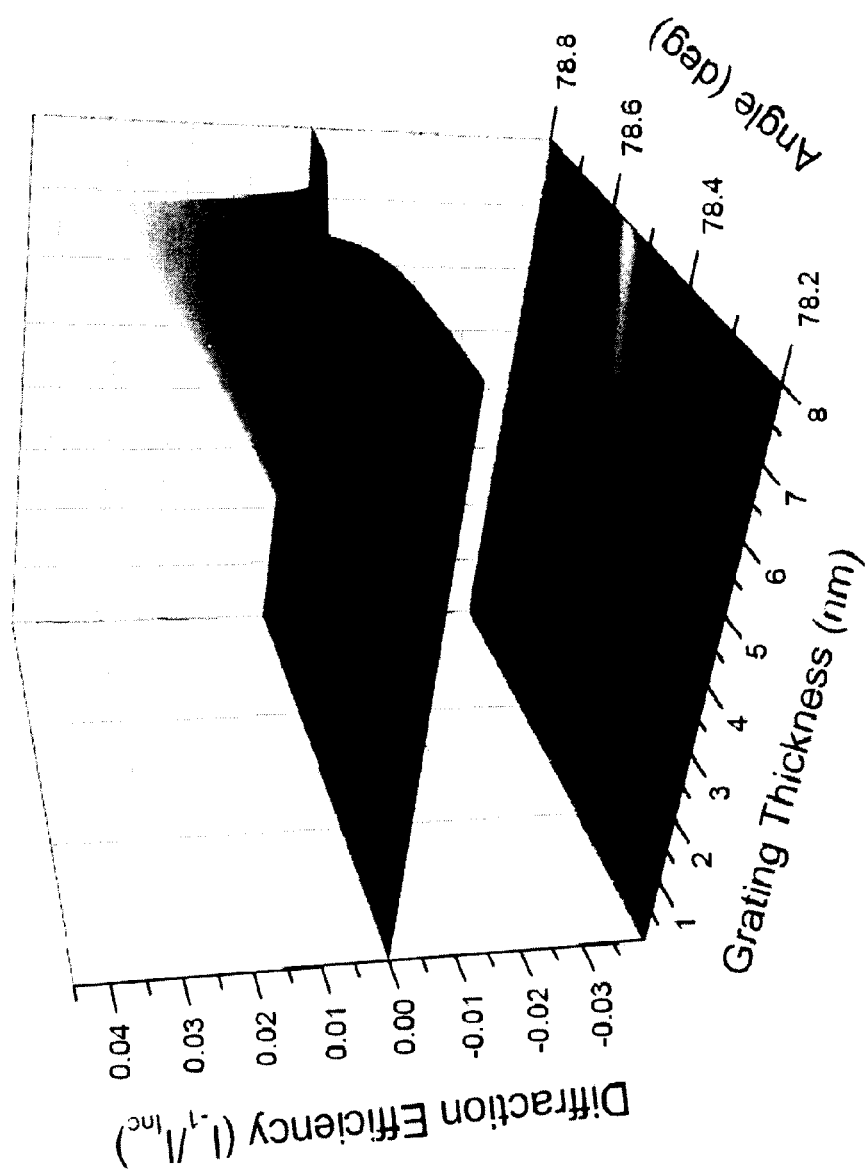
FIG. 7 is a plot of the calculated diffraction efficiency as a function of the grating thickness and the angle of incidence for a-Si$_{1-x}$N$_x$:H multilayer with N=10 and a Corning 7059 substrate (n=1.55). The unit cell is composed of 140 nm of a-Si$_{0.45}$N$_{0.55}$:H and 150 nm of a-Si$_3$N$_4$:H. The first layer is 42 nm of S$_{0.45}$N$_{0.55}$. The number of periods is N=10. We assume TE polarized incident light.

Next, we analyzed the performance of the device as a function of the thicknesses of the grating and the first layer and as a function of the number of periods. FIG. 7 shows a plot of the diffraction efficiency as a function of the angle of incidence and grating thickness, with the grating thickness ranging from 0 nm to 8 nm. While Equation 20 would indicate that for a grating thickness d<<λ, the diffraction intensity should grow quadratically with d, a calculation for a fixed angle showed a more complicated trend. This was due to the fact that the refractive index close to the interface changes as the analyte accumulates on the grating and the BSW resonance deviates from its original position. Even though the grating thickness was increased by only a few nanometers, the effect was significant because of the long interaction time between the incoming light and the protein due to the mode strong field confinement. On the other hand, FIG. 7 shows that, if we follow the BSW resonance, we recover the typical signal quadratic dependence on d, typical of a diffraction-based sensor. In experiments with a grating of about 4 nm in thickness, the thickness variation due to the analyte accumulation is often less than 1 nm, especially when the detection target has a small concentration. In such a situation, the angle deviation can be less then 0.1 degrees. Even if the deviation of the peak is followed, one could employ data acquisition methods to follow the change in the angle of the diffracted peak, which can also occur in any diffraction-based sensor because of temperature and pressure fluctuations (Yu et al., *Anal Chem.* 76: 1971, 2004).

Figure 8:
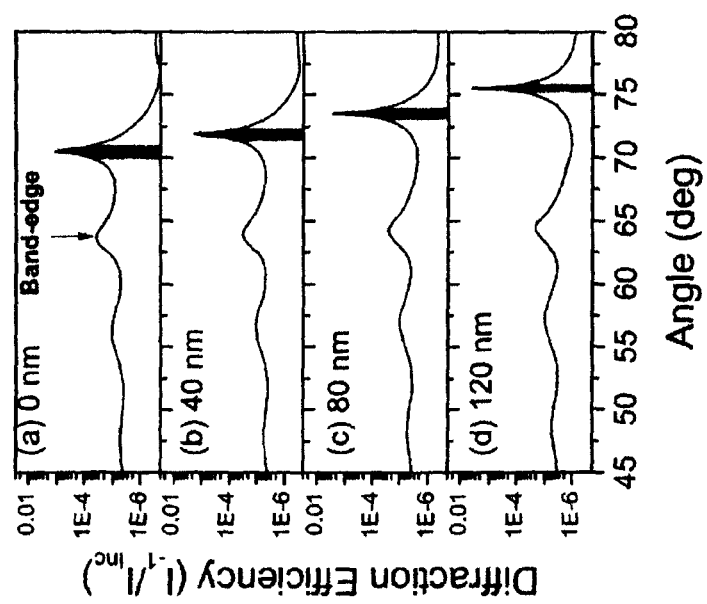
FIG. 8 is a plot of the calculated diffraction efficiency as a function of the angle of incidence for a-Si$_{1-x}$N$_x$:H multilayer on a Corning 7059 substrate (n=1.55). The unit cell is composed of 140 nm of a-Si$_{0.45}$N$_{0.55}$:H and 150 nm of a-Si$_3$N$_4$:H. The number of periods is N=10. We consider four different thicknesses of the first layer: (a) 0 nm, (b) 40 nm, (c) 80 nm, and (d) 120 nm of a-Si$_{0.45}$N$_{0.55}$:H. Peaks associated with BSWs are highlighted.

An important issue for any designed structure is its robustness with respect to any deviation from nominal parameters. We showed, starting from Equation 13, that the thickness of the first layer is important in determining the BSW dispersion relation. In FIG. 8, we plotted the diffraction efficiency of four structures, all with our chosen unit cell, but with different terminations. The first layer (of a-$Si_{0.45}N_{0.55}$) ranged from 0 nm to 120 nm in thickness. Each curve was characterized by more than one peak. The strongest peak was identified with the BSW, while the peaks that were shorter and broader corresponded to the band-edge and other propagating states in the finite dielectric stacks. The largest diffraction enhancement occurred for the surface mode, the position of which was strongly dependent on the multilayer termination. As the thickness of the first layer increased, the BSW peak shifted from the band-edge into the gap where the field confinement was stronger. The resonances became narrower, and the diffraction efficiency increased. A different behavior was observed for the other peaks, the positions of which were determined by the unit cell composition, and they signaled the presence of bulk states of the dielectric stacks. FIG. 8 also shows that the angle of incidence can be a useful tuning parameter to compensate for deviation from the nominal mode position.

EXAMPLE 3

Structure Scheme and Design Parameters of Diffraction-based Sensor with BSW-Enhanced Diffraction In this example, we describe the parameters for the realization of a $Si_{(1-x)}N_x$:H multilayer that supports a BSW, which can be exploited in diffraction-based sensors. The design of the structure is made difficult by the presence of several constraints. First, the diffraction grating has a fixed period of 5 μm. Second, the substrate of the multilayer is a Corning substrate with a refractive index of $n_{coming}$=1.5. Third, the device must operate in water, wherein $n_{H_2O}$=1.33. Fourth, silicon nitride presents a small, but not negligible, absorption at the desired wavelength of λ=670 nm.

The parameters considered when designing the diffraction-based sensor of this example are outlined as follows. The diffraction grating yields a momentum contribution of G=1.25 $\mu m^{-1}$. Accordingly, the diffracted or incident beam must be coupled with the BSW or must be outside the photonic gap. The choice of a large refractive index contrast is not convenient, and the position of the BSW within the gap must be carefully engineered. The device must operate in the Kretschmann configuration, and the incoming and diffracted beam must lie above the Coming light line to prevent exponential decay in the substrate with a strong reduction of diffracted signal. The device must also operate in water; thus, the BSWs exist only below the water light line. Finally, the refractive index and absorption in $Si_{(1-x)}N_x$:H increases with silicon concentration.

Figure 9:
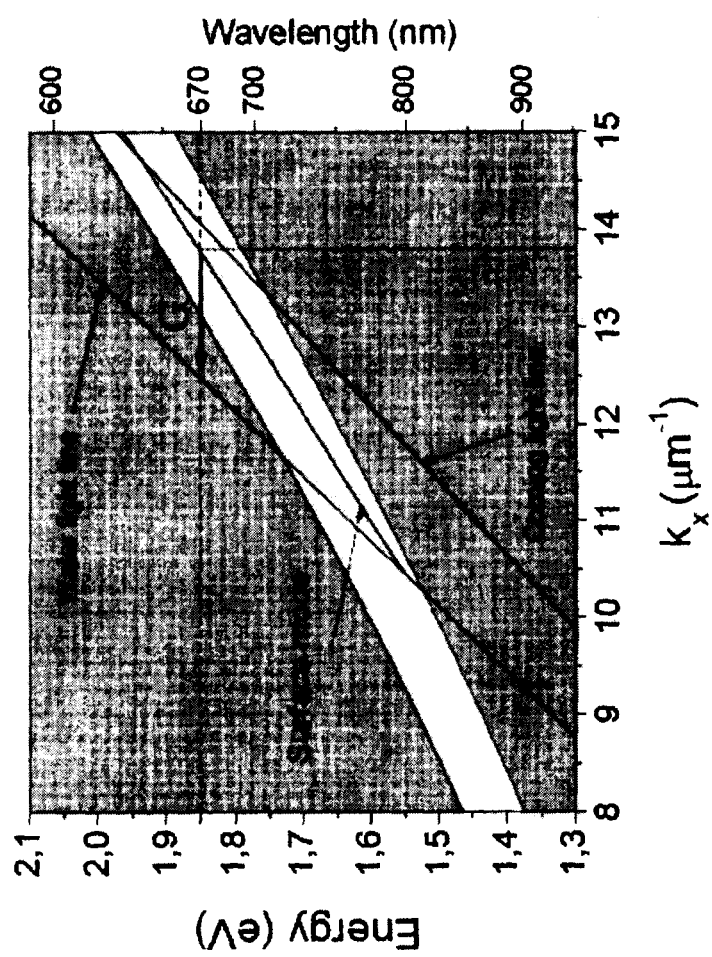
FIG. 9 is a plot of a Bloch surface wave dispersion relation. The vector G indicates the momentum contribution given by a grating of period Λ=5 μm. The white area is the photonic gap region, while the dashed line is at λ=670 nm (1.851 eV), which corresponds to the excitation wavelength.
Figure 10:
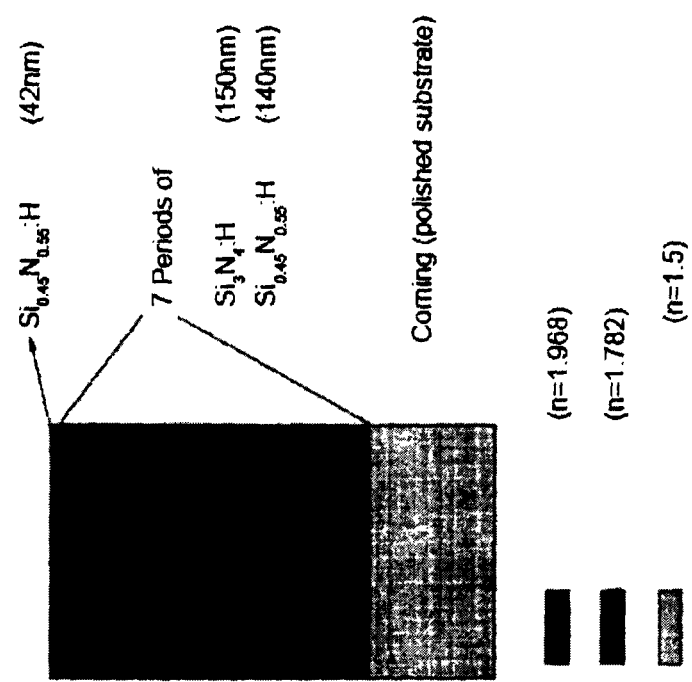
FIG. 10 is a diagram of the structure scheme and design parameters of a multilayered structure.

The diffraction-based sensor of this example included a semi-infinite $Si_{0.45}N_{0.55}/Si_3N_4$ multilayer in water. The BSW dispersion is shown in FIG. 9, together with the photonic band gap dispersion and the light lines of water and the Corning substrate. The corresponding finite structure was composed of seven and a half periods of $Si_{0.45}N_{0.55}/Si_3N_4$. Starting at the top of the device, a $Si_{0.45}N_{0.55}$ layer of 42 nm in thickness was grown on seven periods of $Si_3N_4$ (150 nm in thickness)/$Si_{0.45}N_{0.55}$ (140 nm), and this multilayer was atop a double-polished Corning substrate layer. A sketch of the structure is shown in FIG. 10. The multilayer of this example had a planar dimension of 10 cm×10 cm, but could be cut into smaller pieces with dimensions of, for example, 1 cm×3 cm, upon which the diffraction grating may be printed.

Figure 11:
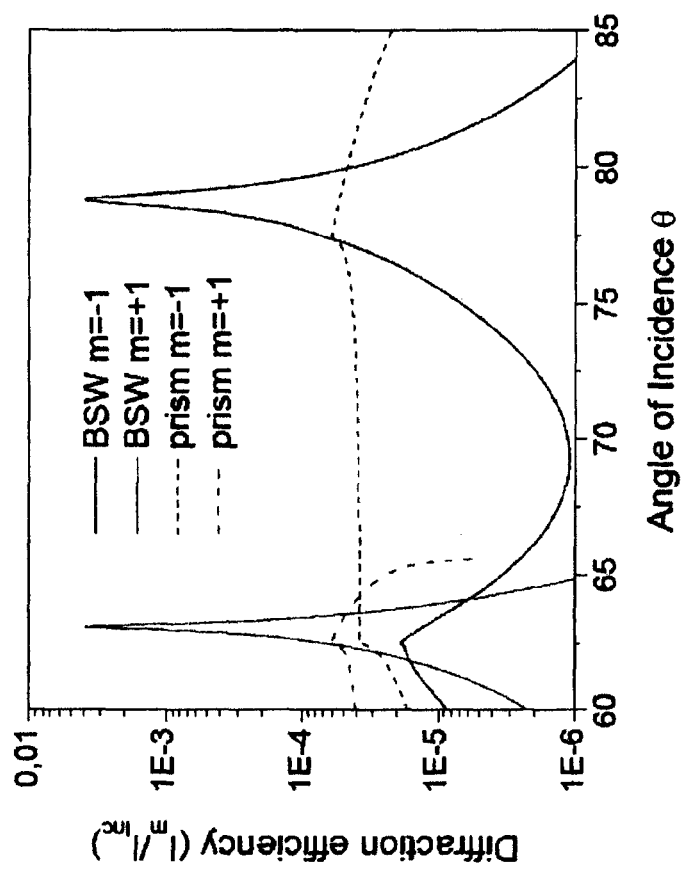
FIG. 11 is a plot of the diffraction efficiency (I$_m$/I$_{Inc}$) as a function of the incidence angle. Two diffraction orders are shown: m=1 and m=−1, in the case of a protein grating of 4 nm thickness placed onto the multilayer and the prism.

Once the grating was printed on the surface of the device, we predicted an enhancement of the diffraction of two orders of magnitude, compared to the case in which the grating is printed directly on the prism. The results of the diffraction enhancement calculations are shown in FIG. 11, where the diffraction efficiency is the ratio between the intensity of the m-th order and the intensity of the incident field. In the case of m=−1, the incident field was coupled to the BSW, and the diffracted beam is outside the gap (as shown in FIG. 9). On the contrary, when m=1, the situation was reversed (e.g., the diffracted beam was coupled to the BSW, but the incident field was not enhanced). This corresponded to the reverse arrow in FIG. 9. In both cases, the diffraction enhancement was the same since the effects of the BSW were simply exchanged between the incident and diffracted beams.

EXAMPLE 4

Diffraction-Based Sensor with BSW-enhanced Diffraction Containing an Immunoglobulin G Diffraction Grating In this example, we describe a diffraction-based sensor with BSW-enhanced diffraction containing an immunoglobulin G diffraction grating.

For a one-dimensional grating of height d and period Λ, the intensity of the m-th order diffracted beam is described by Equation 20. The keys to increasing the diffraction efficiency are: (1) obtaining a strong confinement of the incident field in the grating region and (2) maximizing the extraction efficiency of the diffracted beam. We consider an immunoglobulin G protein grating (with d=4 nm and $n_{grating}$=1.45) in water (n=1.33) on a $Si/SiO_2$ multilayer with a silicon substrate of 600 μm (Angeley et al., *Opt Eng.* 45: 043402, 2006). The composition of the multilayer included the following: Si (53 nm), followed by two and a half periods of $SiO_2$ (324 nm)/Si (267 nm). The incident light was coupled through a ZnSe prism ($n_{prism}$=2.4) in the Kretschmann configuration (see, e.g., FIG. 2b). The diffraction enhancement in the dielectric structure was compared with one calculated for the same grating on the top of a thin gold layer ($d_{Gold}$=40 nm), where a surface plasmon was exploited. The height of the metal layer was optimized to maximize the field localization and to reduce absorption effects on diffraction efficiency. We also calculated the diffraction for the geometry of the same grating placed directly on the surface of the ZnSe prism.

Figure 12:
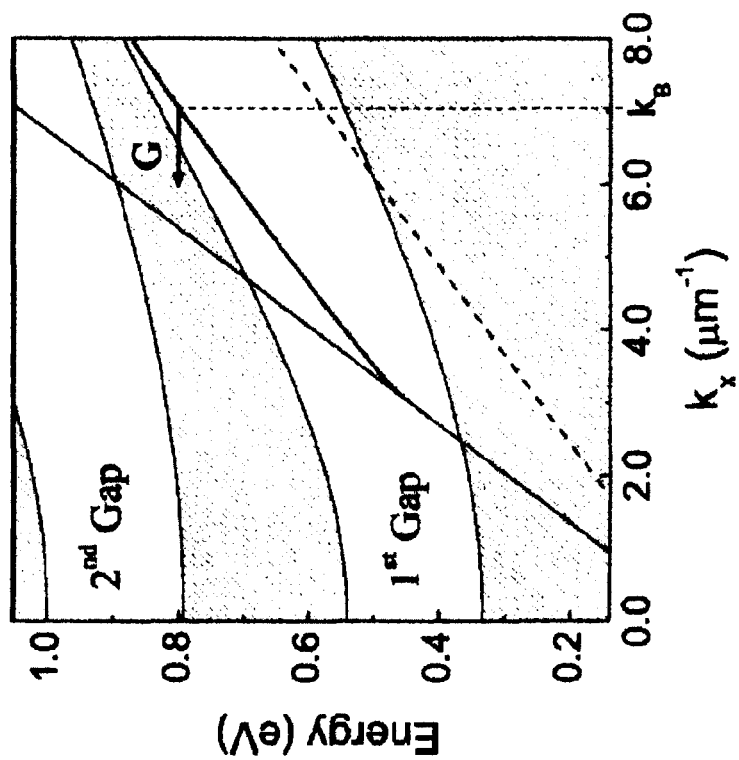
FIG. 12 is a plot of the gap map and BSW dispersion for TE polarization. The solid and dashed lines are water and ZnSe light lines, respectively. The wave vector of the BSW at 0.8 eV (1.55 μm) is indicated with k$_B$. The arrow corresponds to a momentum contribution −G for a 6 μm period one-dimensional grating.

The BSW dispersion relation depends strongly on both the cladding, here assumed to be water, and on the thickness and index of the topmost layer; the amplitude and dispersion of the photonic gap, on the other hand, are determined only by the unit cell materials and composition (Ych et al., *Appl Phys Lett.* 32: 104, 1978; Robertson et al., *Appl Phys Lett.* 74: 1800, 1999; and Yariv et al., *Optical Waves in Crystals*, Wiley, N.J., 2003). We chose to work at the wavelength of $\lambda=1.55$ μm (0.8 eV), which corresponds to a BSW wave number of 7.05 μm. The parameters chosen for our structure produced a BSW that was in a gap, but not too far from a gap edge, as illustrated in FIG. 12. The calculations were completed for a semi-infinite Si/SiO$_2$ periodic multilayer.

Figure 13:
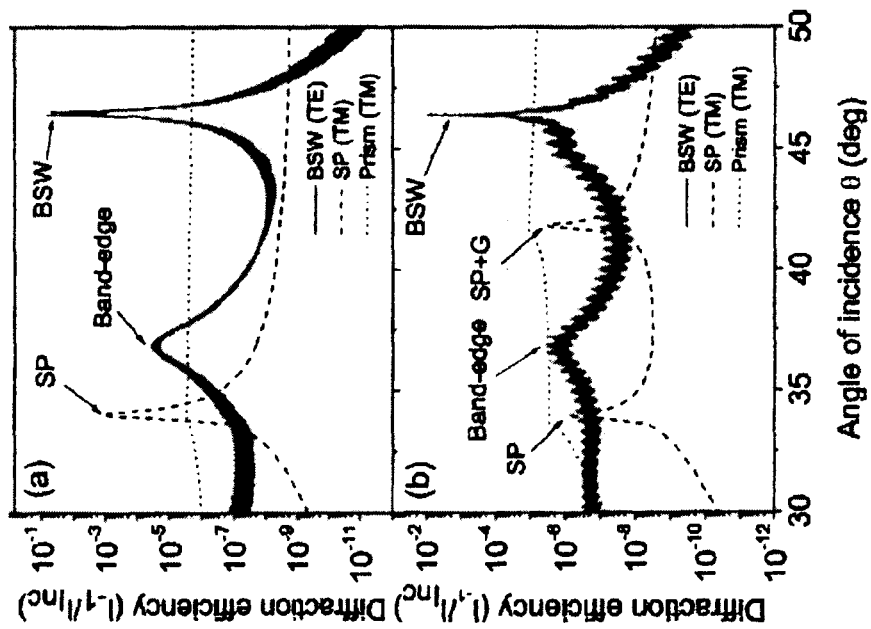
FIG. 13 is a plot of the calculated diffraction efficiency for a 4 nm height one-dimensional grating of (a) 400 and (b) 6 μm periods onto a dielectric multilayer (TE polarization) (solid line), a 40 nm high gold layer (TM polarization) (dashed line), and a ZnSe prism (TM polarization) (dotted line) as a function of the angle of incidence θ at λ=1.55 μm.

First, we considered a long period grating with $\Lambda=400$ μm. The momentum contribution G provided by the grating was very small and, thus, the first-order diffracted beam wave vector component was $k_f \neq k_x$. This choice guaranteed that both incident and diffracted beams would be resonant with the surface mode so that field enhancement and extraction efficiency would be simultaneously maximized (Yu et al., *Anal Chem.* 76: 3530, 2004). In FIG. 13*a*, we plotted the diffraction efficiency for the first-order diffracted beam ($I_{-1}/I_{inc}$) as a function of the incident angle θ, evaluated with a standard Fourier modal method (Whittaker et al., *Phys Rev B* 60: 2610, 1999). For the dielectric multilayer, we observed a strong peak at θ=46°, which corresponded to $k_x=k_B$. Furthermore, another larger peak was found at around θ=37°. This corresponded to a resonant coupling with the Si/SiO$_2$ multilayer band edge, which was also associated with a field enhancement in the whole of the multilayer. The fast oscillations in spectra were due to interference effects in the Si substrate. When the BSW was excited, the diffraction intensity was ~60 times larger than in the metallic system with the surface plasmon wave excited. In both cases, when a surface wave was excited, we predicted an enhancement of several orders of magnitude with respect to a device in which the protein grating was placed on the bare prism.

In the limit of a long period grating, the lower-order diffracted beams have $k_f \neq k_x$, and, therefore, it can be particularly difficult to detect them in the presence of the specularly reflected beam. Higher orders can be considered, but with a large loss of signal intensity. Thus, in certain situations, working with a shorter ($\Lambda-\lambda$) period can be more convenient.

We calculated the diffraction efficiency for the same vertical structures as in the previous example, but with a grating period $\Lambda=6$ μm. Here, the grating momentum contribution G could not be neglected. In the dielectric system, the diffracted beam was no longer resonant with the BSW, but G was large enough to bring the diffracted beam out of the photonic gap, as shown in FIG. 12. For our choice of parameters, the diffracted beam was still confined by total internal reflection in the multilayer since this region out of the gap was below the water light line.

In FIG. 13*b*, we observed that, even for a shorter period, enhancements associated with the BSW and the band-edge occurred. Nevertheless, the diffraction efficiency was almost one order of magnitude less than in the previous device since the BSW did not increase the extraction efficiency of the diffracted beam. In the surface plasmon case, the diffraction curve presented two peaks. The former was still located at θ=33° and corresponded to the excitation of the surface plasmon wave for the incoming beam; the latter was the result of excitation of the surface plasmon wave by the diffracted beam that occurred at θ=42° when the incident beam was $k_x=k_{SP}+G$. In both cases, the intensity was lower than when the grating was placed directly on the prism because of the absorption losses that affect incident or diffracted beams. The dielectric system showed efficiency greater than the surface plasmon device by two to three orders of magnitude.

Finally, for the BSW structures, any deviations in fabrication from nominal thicknesses of the layers, particularly the topmost layer, led to a small change in the angle of incidence at which the peak in the diffraction efficiency occurred; thus, such deviations can be compensated for by working at an angle slightly different from the nominal value.

Other Embodiments

All publications, patents, and patent applications mentioned in the above specification are hereby incorporated by reference. Various modifications and variations of the described method and system of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the art are intended to be within the scope of the invention.

Other embodiments are in the claims.

What is claimed is:

1. A device for the detection of an analyte in a sample comprising:
    (a) a diffraction grating comprising an immobilized binding agent capable of binding said analyte, and
    (b) a periodic dielectric multilayer, wherein said immobilized binding agent is immobilized on the surface of said periodic dielectric multilayer,
    wherein Bloch surface waves are capable of propagating at the surface of said periodic dielectric multilayer, thereby enhancing diffraction from said diffraction grating.

2. The device of claim 1, wherein said immobilized binding agent comprises protein or nucleic acid.

3. The device of claim 2, wherein said protein is an antibody.

4. The device of claim 3, wherein said antibody is immunoglobulin G (IgG).

5. The device of claim 1, wherein said device further comprises a silicon-based substrate layer.

6. The device of claim 1, wherein said periodic dielectric multilayer comprises between 2 and 20 periods.

7. The device of claim 1, wherein said periodic dielectric multilayer comprises between 2 and 80 layers.

8. The device of claim 1, wherein said periodic dielectric multilayer comprises at least two periods each comprising between 1 and 40 layers.

9. The device of claim 1, wherein said periodic dielectric multilayer comprises at least one layer comprising silicon or silicon dioxide (SiO$_2$).

10. The device of claim 1, wherein said periodic dielectric multilayer comprises at least one layer comprising silicon nitride at a ratio of Si$_{(1-x)}$N$_x$:H.

11. The device of claim 10, wherein said periodic dielectric multilayer comprises at least one layer comprising silicon nitride at a ratio of Si$_3$N$_4$:H.

12. The device of claim 10, wherein said periodic dielectric multilayer comprises at least one layer comprising silicon nitride at a ratio of $Si_{0.45}N_{0.55}$:H.

13. The device of claim 1, wherein said periodic dielectric multilayer comprises 7 periods, wherein each period comprises 2 layers.

14. The device of claim 13, wherein said periods comprise a first layer comprising silicon nitride at a ratio of $Si_3N_4$:H and a second layer comprising silicon nitride at a ratio of $Si_{0.45}N_{0.55}$:H.

15. The device of claim 14, wherein said first layer is about 150 nm in thickness.

16. The device of claim 14, wherein said second layer is about 140 nm in thickness.

17. The device of claim 14, wherein said periodic dielectric multilayer comprises an additional layer.

18. The device of claim 17, wherein said additional layer comprises silicon nitride at a ratio of $Si_{0.45}N_{0.55}$:H.

19. The device of claim 17, wherein said additional layer is about 42 nm in thickness.

20. The device of claim 1, wherein said device further comprises a prism base for the Kretschmann configuration.

21. The device of claim 20, wherein said prism is a zinc-selenium prism.

22. The device of claim 1, wherein said periodic dielectric multilayer comprises layers comprising zinc sulfide (ZnS), titanium oxide ($TiO_2$), cerium oxide ($CeO_2$), magnesium fluoride (MgF), cryolite ($Na_3AlF_6$), gallium nitride (GaN), indium tin oxide (ITO), zinc telluride (ZnTe), BeZnTe, MgSe/BeZnTe, InGaAs, indium phosphide (InP), gallium arsenide (GaAs), $Al_xGa_{1-x}As$, GaAsSb, or $Al_xGa_{1-x}N$.

23. The device of claim 1, wherein propagation of Bloch surface waves at the surface of said periodic dielectric multilayer enhances diffraction of visible light from said diffraction grating.

24. The device of claim 1, wherein propagation of Bloch surface waves enhances diffraction of visible light from said diffraction grating.

25. A diffraction-based device comprising:
    (a) a diffraction grating comprising chemical groups capable of immobilizing a binding agent capable of binding to an analyte, and
    (b) a periodic dielectric multilayer,
    wherein Bloch surface waves are capable of propagating at the surface of said periodic dielectric multilayer, thereby enhancing diffraction from said diffraction grating.

26. The device of claim 25, wherein said chemical groups comprise biotin, avidin, streptavidin, protein G, goat anti-mouse-Fc, or amine-reactive groups.

27. The device of claim 25, wherein propagation of Bloch surface waves at the surface of said periodic dielectric multilayer enhances diffraction of visible light from said diffraction grating.

28. The device of claim 25, wherein propagation of Bloch surface waves enhances diffraction of visible light from said diffraction grating.

29. A method for the detection of an analyte in a sample comprising:
    (a) providing a device comprising: (i) a diffraction grating comprising an immobilized binding agent capable of binding said analyte, and (ii) a periodic dielectric multilayer, wherein said immobilized binding agent is immobilized on the surface of said periodic dielectric multilayer;
    (b) contacting the device with said sample, so analyte in said sample binds to said immobilized binding agent; and
    (c) detecting said analyte by Bloch surface wave-enhanced optical diffraction associated with said analyte binding to said immobilized binding agent.

30. The method of claim 29, wherein said Bloch surface-wave enhanced optical diffraction is Bloch surface-wave enhanced optical diffraction of visible light.

31. A method for the detection of an analyte in a sample comprising:
    (a) providing a device comprising (i) a diffraction grating comprising chemical groups capable of immobilizing a binding agent capable of binding to an analyte, and (ii) a periodic dielectric multilayer, wherein Bloch surface waves are capable of propagating at the surface of said periodic dielectric multilayer, thereby enhancing diffraction from said diffraction grating;
    (b) contacting the device with a binding agent, so said binding agent binds to said chemical groups to immobilize said binding agent;
    (c) contacting the device of (b) with said sample, so analyte in said sample binds to said immobilized binding agent; and
    (d) detecting said analyte by Bloch surface wave-enhanced optical diffraction associated with said analyte binding to said immobilized binding agent.

32. The method of claim 31, wherein said Bloch surface-wave enhanced optical diffraction is Bloch surface-wave enhanced optical diffraction of visible light.

* * * * *